United States Patent
Qi et al.

(10) Patent No.: US 11,781,983 B2
(45) Date of Patent: Oct. 10, 2023

(54) ALARM METHOD, SYSTEM AND STORAGE MEDIUM FOR ABNORMALITIES OF SAMPLE ANALYZER

(71) Applicant: Shenzhen Mindray Bio-Medical Electronics Co., Ltd., Shenzhen (CN)

(72) Inventors: Huan Qi, Shenzhen (CN); Wenbo Zheng, Shenzhen (CN); Bo Ye, Shenzhen (CN); Zhaoyang Li, Shenzhen (CN); Yi Ye, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 420 days.

(21) Appl. No.: 17/078,705

(22) Filed: Oct. 23, 2020

(65) Prior Publication Data
US 2021/0041361 A1 Feb. 11, 2021

Related U.S. Application Data

(63) Continuation of application No. PCT/CN2019/084686, filed on Apr. 26, 2019.

(30) Foreign Application Priority Data

Apr. 28, 2018 (WO) ................ PCT/CN2018/085198

(51) Int. Cl.
  *G01N 33/80* (2006.01)
  *G01N 15/14* (2006.01)
  (Continued)

(52) U.S. Cl.
  CPC ......... *G01N 21/6428* (2013.01); *G01N 15/06* (2013.01); *G01N 15/1429* (2013.01);
  (Continued)

(58) Field of Classification Search
  None
  See application file for complete search history.

(56) References Cited

U.S. PATENT DOCUMENTS

| 5,891,734 A * | 4/1999 | Gill ...................... G01N 35/109 436/805 |
| 6,525,807 B1 * | 2/2003 | Morikawa .............. G01N 21/47 356/336 |

(Continued)

FOREIGN PATENT DOCUMENTS

| CN | 1549925 A | 11/2004 |
| CN | 101750476 A | 6/2010 |

(Continued)

OTHER PUBLICATIONS

Boulassel et al. (Accuracy of Platelet Counting by Optical and Impedance Methods in Patients with Thrombocytopaenia and Microcytosis, Sultan Qaboos University Med. J., Nov. 2015, vol. 15, pp. e463-e468) (Year: 2015).*

(Continued)

*Primary Examiner* — Jill A Warden
(74) *Attorney, Agent, or Firm* — Kory D. Christensen

(57) ABSTRACT

A method, system and storage medium for providing an alarm for indicating that an abnormality is present in a sample analyzer are provided. The method includes: mixing a first aliquot of a blood sample with a diluent agent to prepare a first test sample; mixing a second aliquot of the blood sample with a lytic reagent to prepare a second test sample; detecting electrical impedance signals of the first test sample; detecting at least two types of optical signals of the second test sample; acquiring first platelet detection data based on the electrical impedance signals; acquiring second platelet detection data based on the at least two types of optical signals; acquiring an evaluation result based on a difference between the first platelet detection data and the (Continued)

second platelet detection data; determining whether the evaluation result meets a preset condition to provide an alarm.

14 Claims, 12 Drawing Sheets

(51) Int. Cl.
  *G01N 15/00* (2006.01)
  *G01N 21/64* (2006.01)
  *G01N 15/06* (2006.01)
  *G01N 21/47* (2006.01)
  *G01N 27/02* (2006.01)
  *G01N 33/487* (2006.01)
  *G08B 21/18* (2006.01)

(52) U.S. Cl.
  CPC ......... *G01N 15/1436* (2013.01); *G01N 21/47* (2013.01); *G01N 27/02* (2013.01); *G01N 33/48707* (2013.01); *G01N 33/80* (2013.01); *G08B 21/185* (2013.01); *G01N 15/1404* (2013.01); *G01N 2015/008* (2013.01); *G01N 2015/0069* (2013.01); *G01N 2015/0084* (2013.01); *G01N 2015/0693* (2013.01); *G01N 2015/1402* (2013.01); *G01N 2021/6439* (2013.01)

(56) References Cited

U.S. PATENT DOCUMENTS

| 2003/0138871 | A1  | 7/2003 | Shine et al.       |
|--------------|-----|--------|--------------------|
| 2005/0079623 | A1  | 4/2005 | Ortiz et al.       |
| 2006/0160229 | A1* | 7/2006 | Lopez ........... G01N 15/12 |
|              |     |        | 436/63             |
| 2007/0105230 | A1  | 5/2007 | Perez et al.       |

FOREIGN PATENT DOCUMENTS

| CN | 103471980  | A | 12/2013 |
| CN | 103471982  | A | 12/2013 |
| CN | 103472034  | A | 12/2013 |
| CN | 103472216  | A | 12/2013 |
| CN | 103941026  | A | 7/2014  |
| CN | 104458540  | A | 3/2015  |
| CN | 104458541  | A | 3/2015  |
| CN | 104541149  | A | 4/2015  |
| CN | 106687810  | A | 5/2017  |
| CN | 107525758  | A | 12/2017 |
| JP | 2000275163 | A | 10/2000 |

OTHER PUBLICATIONS

China National Intellectual Property Administration, Chinese Application No. 201910522216.7, Office Action dated Nov. 2, 2022, 11 pages.

* cited by examiner

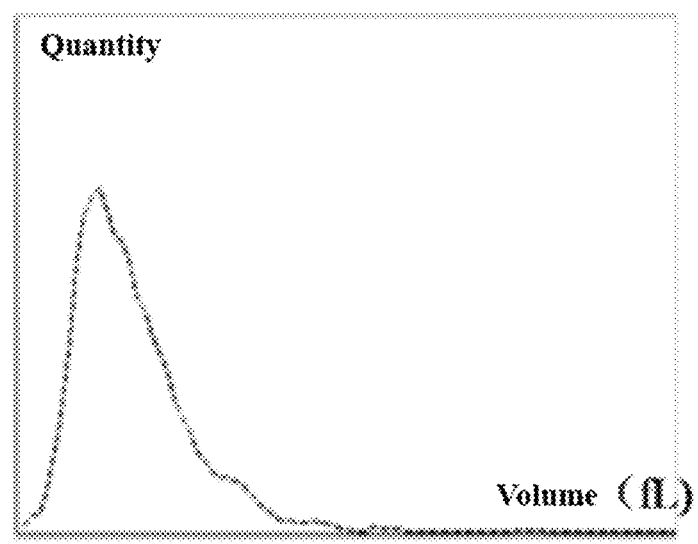
Fig. 6B
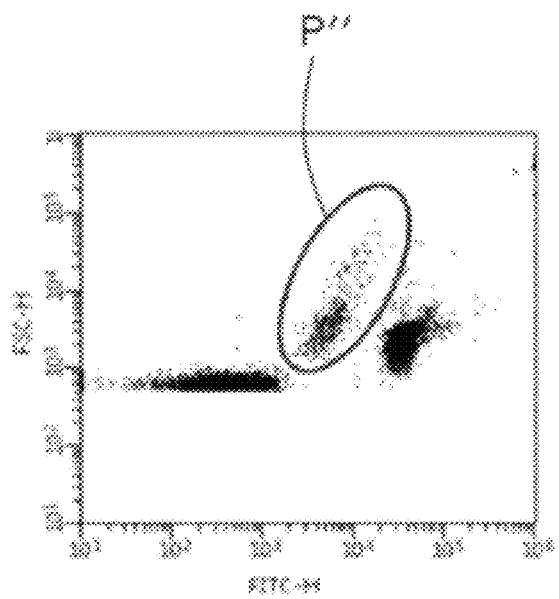 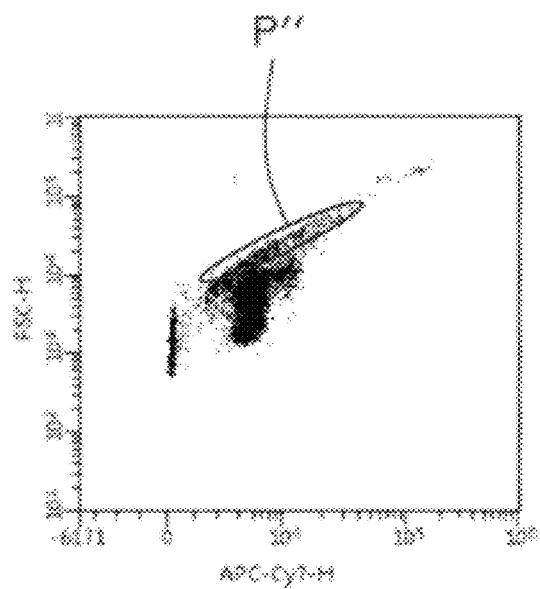
Fig. 7A　　　　　　　　　　Fig. 7B

ALARM METHOD, SYSTEM AND STORAGE MEDIUM FOR ABNORMALITIES OF SAMPLE ANALYZER

CROSS-REFERENCE

This application is a continuation of International Application No. PCT/CN2019/084686, filed Apr. 26, 2019, which claims priority benefit of International Application No. PCT/CN2018/085198, filed Apr. 28, 2018, both of which are incorporated herein by reference.

TECHNICAL FIELD

The present disclosure relates to the field of in vitro detection, and in particular, to a blood analyzer, a blood analysis system and an analysis method for a blood sample and a storage medium thereof.

BACKGROUND ART

Blood analysis is widely used in medical research and detection to acquire related information about blood cells including red blood cells, white blood cells, platelets, etc. Commonly used automated blood analyzers generally analyze blood cells in blood samples based on the electrical impedance principle (also known as Coulter Principle). According to the electrical impedance principle, when particles suspended in an electrolyte pass through a detection aperture with the electrolyte, the equivalent resistance across the detection aperture will change. Under effect of a constant current source cross the detection aperture, the voltage across the detection aperture will change. The changes in the voltage across the detection aperture are collected by a circuit system, and voltage pulse waveforms can thus be generated, wherein amplitudes of the pulse waveforms reflect volume sizes of the particles. The analyzers can provide information about volume distribution of particles in samples according to the acquired pulse waveforms. For blood samples, the blood analyzers can provide a volume distribution histogram of blood cells in a test blood sample based on the electrical impedance principle, and then acquire blood analysis data such as cell classification, cell count and the like by analyzing the volume distribution histogram.

However, detection signals based on the electrical impedance principle can only reflect information about volume of particles passing through the detection aperture, and cannot be used to differentiate among different particles with a same or similar volume. For example, blood cell analysis methods based on the electrical impedance method cannot be used to differentiate among large platelets, red blood cell fragments (schistocytes) and microcytes with a similar volume, and the blood analyzers may mistakenly count a large platelet with relatively large volume as a red blood cell, resulting in false decrease in large platelet detection results, and the blood analyzers may also mistakenly count a red blood cell with relatively small volume (such as a red blood cell fragment and a microcyte) as a platelet, resulting in false increase in platelet detection results. Moreover, in the automated detection process for a large number of blood samples, insufficient cleaning of the detection channel between detections of different blood samples may also affect detection results of platelets. For example, impurity particles attached to the detection channel or uncleaned schistocytes from previous measured sample may be mixed with the present test blood sample, causing a false increase in platelet detection results.

In some cases, platelets may be easily activated and attached to the detection channel, causing a false increase in platelet detection results.

SUMMARY OF THE INVENTION

An aspect of embodiments of the present disclosure includes an alarm method for providing an alarm for indicating that an abnormality is present in a sample analyzer, the method including: providing a blood sample; mixing a first aliquot of the blood sample with a diluent agent to obtain a first test sample for first platelet detection; mixing a second aliquot of the blood sample with a lytic reagent to obtain a second test sample for second platelet detection, wherein red blood cells in the second test sample are lysed; detecting electrical impedance signals of the first test sample; detecting at least two types of optical signals of the second test sample; acquiring first platelet detection data of the blood sample based on the electrical impedance signals; acquiring second platelet detection data of the blood sample based on the at least two types of optical signals; acquiring an evaluation result based on a difference between the first platelet detection data and the second platelet detection data; determining whether the evaluation result meets a preset condition; and providing an alarm for indicating that an abnormality is present in the first platelet detection and/or an abnormality is present in the step of electrical impedance signal detection of the sample analyzer, when the evaluation result meets the preset condition.

Acquiring second platelet detection data of the blood sample based on the at least two types of optical signals may include: generating a scattergram of the second test sample based on the at least two types of optical signals; differentiating a white blood cell region from a platelet region in the scattergram based on the at least two types of optical signals; and acquiring the second platelet detection data of the blood sample based on the platelet region.

The alarm method provided by embodiments of the present disclosure may include: outputting a prompt that the abnormality of the first platelet detection is caused by the abnormality in the step of the electrical impedance signal detection and/or that the first platelet detection result is unreliable.

Further, in the alarm method provided by embodiments of the present disclosure, the lytic reagent includes a hemolytic agent for lysing red blood cells and a fluorescence dye for staining blood cells, and the at least two types of optical signals include forward scattered light signals and fluorescent signals.

Further, in the alarm method provided by embodiments of the present disclosure, the lytic reagent comprises a hemolytic agent for lysing red blood cells, and the at least two types of optical signals comprise first scattered light signals and second scattered light signals, wherein the first scattered light signals are forward scattered light signals, and the second scattered light signal are at least one type of medium-angle scattered light signals and side scattered light signals.

Further, in the alarm method provided by embodiments of the present disclosure, acquiring the second platelet detection data of the blood sample based on the platelet region includes: acquiring a derived platelet volume histogram based on the forward scattered light signals of a particle population in the platelet region; or acquiring the second platelet detection data of the blood sample based on a number of particles in the platelet region.

Further, in the alarm method provided by embodiments of the present disclosure, the lytic reagent includes a hemolytic agent for lysing red blood cells and a fluorescence dye for staining blood cells, the at least two types of optical signals include side scattered light signals and fluorescent signals; and the second platelet detection data of the blood sample is acquired based on a number of particles in the platelet region.

Further, in the alarm method provided by embodiments of the present disclosure, the platelet region includes a large platelet region, and the second platelet detection data of the blood sample is acquired by using the large platelet region.

Further, in the alarm method provided by embodiments of the present disclosure, the first platelet detection data includes at least one characteristic parameter of first platelet volume distribution data, and the second platelet detection data includes at least one characteristic parameter of second platelet volume distribution data.

Further, in the alarm method provided by embodiments of the present disclosure, the characteristic parameter is selected from one or more of a platelet count, a platelet volume histogram, a mean platelet volume and a platelet volume distribution width; or the characteristic parameter is selected from one or more of a platelet count, a platelet volume histogram, a mean platelet volume and a platelet volume distribution width within a certain volume threshold range.

Further, in the alarm method provided by embodiments of the present disclosure, the two types of optical signals include scattered light signals and fluorescent signals, and the method further includes classifying white blood cells into white blood cell subpopulations, or counting white blood cells or identifying nucleated red blood cells or immature cells or basophils according to the scattered light signals and the fluorescent signals.

Further, in the alarm method provided by embodiments of the present disclosure, the two types of optical signals include first scattered light signals and second scattered light signals, wherein the first scattered light signals are forward scattered light signals, and the second scattered light signals are at least one type of the medium-angle scattered light signals and side scattered light signals, and the method further includes classifying white blood cells into white blood cell subpopulations or identifying basophils according to the first scattered light signals and the second scattered light signals.

Further, in the alarm method provided by embodiments of the present disclosure, determining whether the evaluation result meets a preset condition includes: comparing the first platelet detection data with the second platelet detection data to obtain a graphic difference degree therebetween, determining whether the graphic difference degree meets a preset condition; or acquiring numerical information of the first platelet detection data and the second platelet detection data, calculating an evaluation value by using the numerical information, wherein the evaluation value is used to reflect a difference degree between the first platelet detection data and the second platelet detection data; and determining whether the evaluation value meets a preset condition.

Further, the alarm method provided by embodiments of the present disclosure further includes the following steps: outputting the first platelet detection data if there is no alarm for abnormality; or outputting the second platelet detection data if there is an alarm for abnormality.

Further, the alarm method provided by embodiments of the present disclosure may include continuously recording and counting determination results of evaluation values of platelet detection for a plurality of blood samples, and providing an alarm for indicating that an abnormality is present in the electrical impedance signal detection when the continuous determination results of the plurality of blood samples are yes.

An aspect of embodiments of the present disclosure includes a non-volatile computer-readable storage medium with a computer program stored thereon, wherein the computer program, when executed by a processor, implements steps of any alarm method mentioned above.

An aspect of embodiments of the present disclosure includes a blood analysis system, including: a sample treatment device comprising at least one mixing chamber for mixing a first aliquot of a blood sample with a diluent agent to prepare a first test sample for first platelet detection, and for mixing a second aliquot of the blood sample with a lytic reagent to prepare a second test sample for second platelet detection, wherein red blood cells in the second test sample are lysed; a sample detection device comprising an electrical impedance detection unit and an optical detection unit, wherein the electrical impedance detection unit includes an aperture and an electrical impedance detector, and the electrical impedance detector is configured to detect electrical impedance signals of the first test sample passing through the aperture, and the optical detection unit includes an optical flow chamber, a light source and an optical detector, wherein the optical flow chamber is in fluid communication with the mixing chamber, the light source is configured to direct a light beam to the optical flow chamber, and the optical detector is configured to detect at least two types of optical signals of the second test sample passing through the optical flow chamber; a data analysis module comprising a signal acquisition module, a classification and counting module and an alarm module; wherein the signal acquisition module is configured to acquire the electrical impedance signals of the first test sample and the at least two types of optical signals of the second test sample; the classification and counting module is configured to acquire first platelet detection data of the blood sample based on the electrical impedance signals, generate a scattergram of the second test sample based on the at least two types of optical signals, differentiate a white blood cell region from a platelet region in the scattergram based on the at least two types of optical signals, and acquire second platelet detection data of the blood sample based on the platelet region; and the alarm module is configured to acquire an evaluation result based on a difference between the first platelet detection data and the second platelet detection data, determine whether the evaluation result meets a preset condition, and provide an alarm for indicating that an abnormality is present in the first platelet detection and/or an abnormality is present in the electrical impedance detection unit, when the evaluation result meets the preset condition.

Further, in the blood analysis system provided by embodiments of the present disclosure, the classification and counting module is configured to: generate a scattergram of the second test sample based on the at least two types of optical signals; differentiate a white blood cell region from a platelet region in the scattergram based on the at least two types of optical signals; and acquire the second platelet detection data of the blood sample based on the platelet region.

Further, in the blood analysis system provided by embodiments of the present disclosure, the alarm module is configured to output a prompt that the abnormality of the first platelet detection is caused by the abnormality in the electrical impedance detection unit and/or that the first platelet detection result is unreliable.

Further, in the blood analysis system provided by embodiments of the present disclosure, the lytic reagent includes a hemolytic agent for lysing red blood cells and a fluorescence dye for staining blood cells, the at least two types of optical signals include forward scattered light signals and fluorescent signals, and the optical detection unit includes at least one scattered light detector and at least one fluorescent detector.

Further, in the blood analysis system provided by embodiments of the present disclosure, the dissolution reagent includes a hemolytic agent for lysing red blood cells, and the at least two types of optical signals include first scattered light signals and second scattered light signals, wherein the first scattered light signals are forward scattered light signals, and the second scattered light signals are at least one type of medium-angle scattered light signals and side scattered light signals, and the optical detection unit includes at least two scattered light detectors.

Further, in the blood analysis system provided by embodiments of the present disclosure, the classification and counting module is configured to acquire a derived platelet volume histogram based on at least the forward scattered light signals of a particle population in the platelet region; or the classification and counting module is configured to acquire the second platelet detection data of the blood sample based on a number of particles in the platelet region.

Further, in the blood analysis system provided by embodiments of the present disclosure, the lytic reagent includes a hemolytic agent for lysing red blood cells and a fluorescence dye for staining blood cells, the at least two types of optical signals include side scattered light signals and fluorescent signals; and the classification module is configured to acquire the second platelet detection data of the blood sample based on a number of particles in the platelet region.

Further, in the blood analysis system provided by embodiments of the present disclosure, the platelet region includes a large platelet region, the second platelet detection data includes second large platelet data, and the second platelet detection data of the blood sample is acquired by using the large platelet region.

Further, in the blood analysis system provided by embodiments of the present disclosure, the first platelet detection data includes at least one characteristic parameter of first platelet volume distribution data, and the second platelet detection data includes at least one characteristic parameter of second platelet volume distribution data.

Further, in the blood analysis system provided by embodiments of the present disclosure, the characteristic parameter is selected from one or more of a platelet count, a platelet volume histogram, a mean platelet volume and a platelet volume distribution width; or the characteristic parameter is selected from one or more of a platelet count, a platelet volume histogram, a mean platelet volume and a platelet volume distribution width within a certain volume threshold range.

Further, in the blood analysis system provided by embodiments of the present disclosure, the two types of optical signals include scattered light signals and fluorescent signals, and the classification and counting module is further configured to classify white blood cells into white blood cell subpopulations, or count white blood cells or identify nucleated red blood cells or immature cells or basophils according to the scattered light signals and the fluorescent signals.

Further, in the blood analysis system provided by embodiments of the present disclosure, the two types of optical signals include first scattered light signals and second scattered light signals, wherein the first scattered light signals are forward scattered light signals, and the second scattered light signals are at least one type of medium-angle scattered light signals and side scattered light signals, and the classification and counting module is further configured to classify white blood cells into white blood cell subpopulations or identify basophils according to the first scattered light signals and the second scattered light signals.

Further, in the blood analysis system provided by embodiments of the present disclosure, the alarm module is configured to: compare the first platelet detection data with the second platelet detection data to obtain a graphic difference degree therebetween, determine whether the graphic difference degree meets a preset condition; or acquire numerical information of the first platelet detection data and the second platelet detection data, calculate an evaluation value by using the numerical information, wherein the evaluation value is used to reflect a difference degree between the first platelet detection data and the second platelet detection data; and determine whether the evaluation value meets a preset condition.

Further, the blood analysis system provided by embodiments of the present disclosure further includes a user interface for: outputting the first platelet detection data if there is no alarm for abnormality; or outputting the second platelet detection data if there is an alarm for abnormality.

The method and system and the storage medium provided by the present disclosure can provide users with more abundant detection information, and remind users to perform a reexamination or recheck on platelet detection data having an abnormality, thereby increasing accuracy of platelet detection.

BRIEF DESCRIPTION OF THE DRAWINGS

FIG. 6B is a derived volume histogram acquired based on the platelet region P' in FIG. 6A.

FIG. 7A is a forward scattered light (FSC)—fluorescence (FL) scattergram of a second test sample stained by Alexa Fluor 488 dye. FIG. 7B is an FSC-FL scattergram of a second test sample stained by Mitotracker Red dye.

Figure 1:
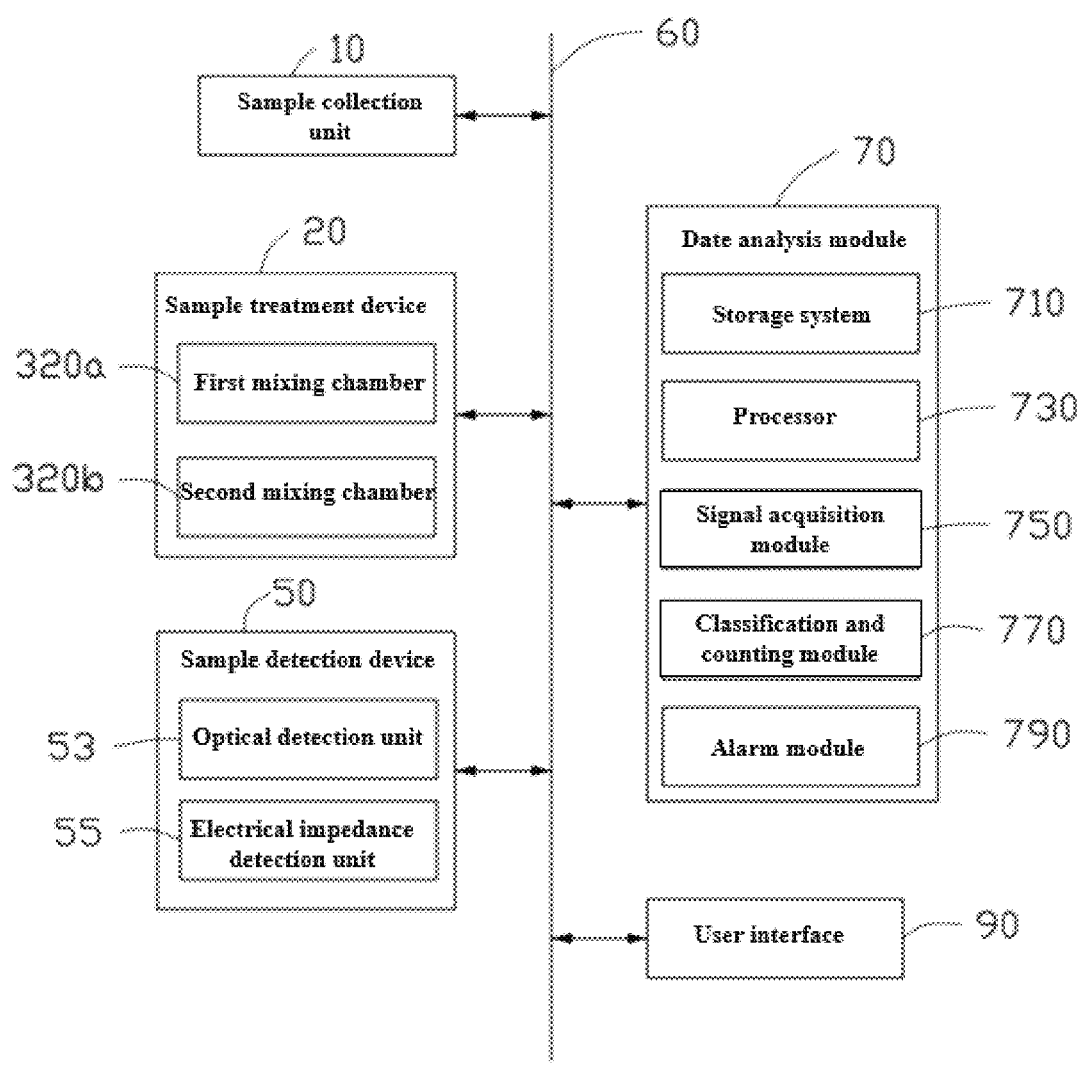
FIG. 1 is a schematic diagram of function modules of a blood analysis system provided by the present disclosure.

| List of Reference numerals | |
|---|---|
| Sample collection unit | 10 |
| Sample treatment device | 30 |
| Mixing chamber | 320, 320a, 320b |
| Sample detection device | 50 |
| Electrical impedance detection unit | 51 |
| Aperture | 512 |
| Electrical impedance detector | 514 |
| Optical detection unit | 53 |
| Optical flow chamber | 532 |
| Light source | 534 |
| Optical detector | 536 |
| Bus | 60 |
| Data analysis module | 70 |
| Storage system | 710 |
| Processor | 730 |
| Signal acquisition module | 750 |
| Classification and counting module | 770 |
| Alarm module | 790 |
| User interface | 90 |
| First housing | 100 |
| Second housing | 200 |

The present disclosure will be further illustrated by the following detailed embodiments in combination with the drawings.

DETAILED DESCRIPTION OF EMBODIMENTS

The technical solution of the present disclosure will be described below with reference to preferred implementations and embodiments of the present disclosure. It should be noted that when one unit is described as being "connected" to another unit, it may be directly connected to another unit or an intermediate unit may exist at the same time. When one unit is described as being "arranged" on another unit, it may be directly arranged on another unit or an intermediate unit may exist at the same time. Unless otherwise defined, all technical and scientific terms used herein have the same meaning as commonly understood by those skilled in the art to which this disclosure belongs. Names of elements or apparatuses used in the specification of the present disclosure are only intended to illustrate the specific embodiments instead of limiting the present disclosure.

A first aspect of the present disclosure relates to a method, system and storage medium for providing an alarm for indicating an abnormality of platelet detection and/or an abnormality of impedance channel by using electrical impedance signals, scattered light signals and fluorescent signals of a blood sample.

FIG. 1 is a schematic diagram of a blood analysis system. The blood analysis system includes a sample collection unit 10, a sample treatment device 30, a sample detection device 50, a data analysis module 70 and a user interface 90. The blood analysis system is provided with a liquid flow system (not shown in the figure), which is configured to make the sample collection unit 10, the sample treatment device 30 and the sample detection device 50 in fluid communication for fluid transfer.

The sample collection unit 10 is configured to supply a blood sample to the sample treatment device 30. The sample treatment device 30 is configured to treat the blood sample for preparing a test sample, and supply the test sample to the sample detection device 50. The sample treatment device 30 may include one or more mixing chambers for preparing the test blood sample into one or more test samples. The sample detection device 50 is configured to detect characteristics of particles in each test sample, and to acquire corresponding detection signals. The data analysis module 70 may be, directly or indirectly, connected electrically with the sample collection unit 10, the sample treatment device 30, the sample detection device 50 and the user interface 90 via a bus 60 to transmit and exchange data or signals.

In a first exemplary implementation of the present disclosure, the sample treatment device 30 includes at least one mixing chamber, which is configured to mix a first aliquot of the test blood sample with a diluent agent to obtain a first test sample, and after cleaning to mix a second aliquot of the test blood sample with a lytic reagent to obtain a second test sample. Alternatively, the sample treatment device 30 may further include a sample dispenser, which is configured to dispense the test blood sample into several aliquots. Each aliquot of blood sample is transferred to the same mixing chamber or different mixing chambers and then treated for subsequent detection. Alternatively, the sample treatment device 30 includes a first mixing chamber 320a and a second mixing chamber 320b for respectively preparing the first test sample and the second test sample. Alternatively, the sample treatment device 30 may include only one mixing chamber for preparing the first test sample and the second test sample one after another.

Specifically, the diluent agent for preparing the first test sample is generally used for diluting blood samples to detect red blood cells and platelets by automated blood analyzers. The diluent agent generally includes one or more salts, such as an alkali metal salt, and is adjusted to be isotonic to maintain volumes of red blood cells. In the implementation of the present disclosure, commercially available diluent agents may be used to dilute the first aliquot of the blood sample to form the first test sample. The commercially available diluent agents include but not limited to M-68DS diluent agent, M-53D diluent agent, etc. which are produced by Shenzhen Mindray Bio-Medical Electronics Co., Ltd. (Shenzhen, China). Temperature and/or stirring conditions for preparing the first test sample may be the same as or similar to sample preparation conditions used by existing automated blood analyzers for detecting red blood cells and platelets.

Specifically, in the first aspect of the present disclosure, the lytic reagent includes a hemolytic agent and a fluorescence dye. The hemolytic agent may be any one of existing hemolytic agents for classifying white blood cells by automated blood analyzers, wherein the hemolytic agent may be any one of a cationic surfactant, a nonionic surfactant, an anionic surfactant and an amphiphilic surfactant or any combination thereof. The fluorescence dye is used for staining blood cells. In some embodiments of the implementation, the fluorescence dye may be a nucleic acid dye, thereby classifying nucleated blood cells, such as white blood cells or nucleated red blood cells, and other types of cells by measuring the differences in scattered light signals and fluorescent signals. In an embodiment of the implementation, the lytic reagent may be prepared by using the lytic reagent formula disclosed in U.S. Pat. No. 8,367,358, the entire disclosure of which is incorporated herein by reference. The lytic reagent disclosed in U.S. Pat. No. 8,367,358 includes a cationic cyanine compound (a fluorescence dye), a cationic surfactant, a nonionic surfactant and an anionic compound. The lytic reagent may be used to lyse red blood cells and classify white blood cells into their subpopulations by detecting differences in scattered light intensities and fluorescence intensities. Other existing fluorescence dyes may also be used in the lytic reagent, for example, the fluorescence dye described in U.S. Pat. No. 8,273,329, the entire disclosure thereof is incorporated herein by reference, such a reagent may be adopted to lyse red blood cells and identify nucleated red blood cells by detecting differences in fluorescence intensities and scattered light intensities. Those skilled in the art may understand that the fluorescence dye may be contained in a separate staining solution, and such a staining solution can be used together with the hemolytic agent without a fluorescence dye. The staining solution may be added to the blood sample in the mixing chamber 320 before, after or upon the hemolytic agent is added for preparing the second test sample. Temperature and/or stirring conditions for preparing the second test sample may be the same as or similar to sample preparation conditions used by existing automated blood analyzers for classifying white blood cells.

Figure 2:
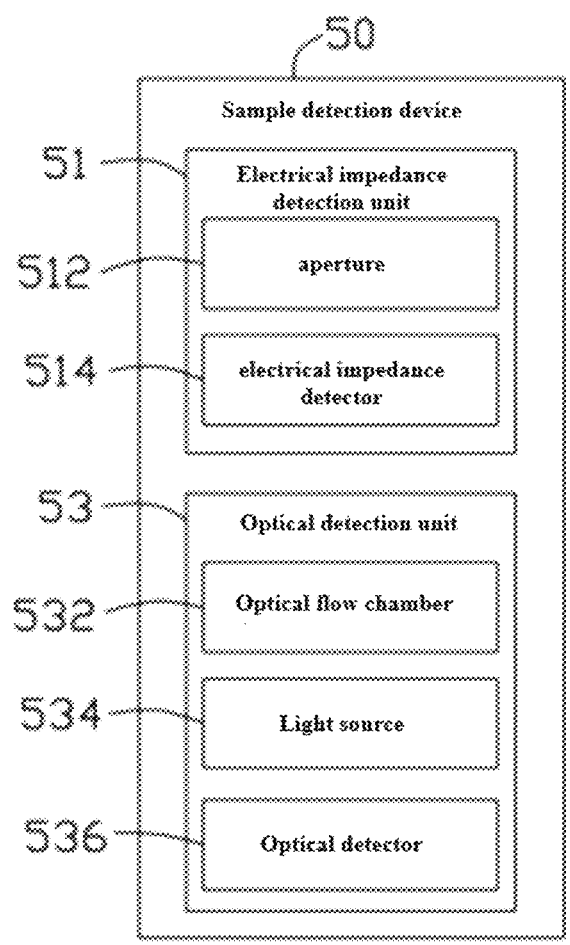
FIG. 2 is a schematic diagram of function modules of a sample detection device of the blood analysis system shown in FIG. 1.

In the first exemplary implementation, the sample detection device 50 of the blood analysis system includes an electrical impedance detection unit 51 and an optical detection unit 53. FIG. 2 is a schematic diagram of function modules of the sample detection device 50.

The electrical impedance detection unit 51 is configured to detect electrical impedance signals of the first test sample. The electrical impedance detection unit 51 includes an aperture 512 and an electrical impedance detector 514. The electrical impedance detector 514 is configured to detect electrical impedance signals of the first test sample when passing through the aperture, such as direct current (DC) impedance signals. It can be understood that, when a particle (or a blood cell) suspended in a conductive solution passes through the aperture, an electrical impedance signal can be detected due to impedance change. The shape, amplitude and width of the pulse generated by the electrical impedance signal are directly related to the size or volume of the particle, and can be converted into the volume of the subject particle. When two or more types of particles with different sizes are detected, a frequency histogram acquired by an electrical impedance detection can reflect a size distribution of these particles. In the prior art, U.S. Pat. Nos. 2,656,508 and 3,810,011 describe methods for automatically detecting blood cells by a blood analyzer provided with an electrical impedance unit, the entire disclosure of which is incorporated herein by reference.

The optical detection unit 53 includes a sheath flow system, an optical flow chamber 532, a light source 534, an optical detector 536 and a corresponding detection circuit. The optical flow chamber 532 is operatively in fluid communication with the mixing chamber 320, so that the first test sample is transferred by the sheath flow system from the mixing chamber 320 to the optical flow chamber 532. The light source 534 is configured to direct a light beam to the optical flow chamber 532. The optical detector 536 is configured to detect at least two types of optical signals of the first test sample. In the first exemplary implementation of the present disclosure, the at least two types of optical signals include forward scattered light signals and fluorescent signals. In an embodiment, the optical detector 536 of the optical detection unit 53 is set to be suitable for detecting the forward scattered light signals and the fluorescent signals of the first test sample passing through the optical flow chamber 532. In another embodiment, the at least two types of optical signals further include side scattered light signals, and the optical detector 536 is set to be suitable for detecting the forward scattered light signals, the side scattered light signals and the fluorescent signals of the first test sample passing through the optical flow chamber 532.

Herein, the optical flow chamber refers to a focused-flow flow chamber suitable for detecting scattered light signals and fluorescent signals, for example, the optical flow chambers used in existing flow cytometers and blood analyzers. When a particle, such as a blood cell, passes through an orifice of the optical flow chamber, the incident light beam emitted from the light source and directed to the orifice is scattered by the particle in all directions. By arranging an optical detector at one or more angles with regard to the incident light beam, the light scattered by the particle can be detected to acquire scattered light signals. Since different blood cell populations have different light scattering properties, the scattered light signals can be used to differentiate different cell populations. Specifically, the scattered light signals detected near the incident beam are generally referred to as forward scattered light signals or small-angle scattered light signals. In some embodiments, the forward scattered light signals may be detected at an angle range from about 1° to about 10° with respect to the incident beam. In some other embodiments, the forward scattered light signals may be detected at an angle range from about 2° to about 6° with respect to the incident beam. Scattered light signals detected at an angle of about 90° with respect to the incident beam are generally referred to as side scattered light signals. In some embodiments, the side scattered light signals may be detected at an angle range from about 65° to about 115° with respect to the incident beam. Generally, fluorescent signals emitted from blood cells stained by a fluorescence dye may also be detected at an angle of about 90° with respect to the incident beam.

The data analysis module 70 includes a storage system 710 and a processor 730. The storage system 710 may store basic programs and data structures for implementing various functions of the methods disclosed herein. The storage system 710 may include one or more memories and one or more non-transitory computer-readable storage media. The non-transitory computer-readable storage media may include a Hard Disk Drive (HDD), a floppy disk, an optical disk, a Secure Digital Memory Card (SD Card), a flash memory card or the like. The memory may include a primary Random Access Memory (RAM) for storing program instructions and data or a Dynamic RAM (DRAM) and a Read Only Memory (ROM) for storing fixed instructions. The non-transitory computer-readable storage medium stores computer programs for implementing the methods disclosed by the present disclosure. The processor 730 includes, but is not limited to, a Central Processing Unit (CPU), a Micro Controller Unit (MCU) and other devices for interpreting computer instructions and processing data in computer software. The processor 730 is configured to execute various computer programs in the non-transitory computer-readable storage medium, thereby enabling the blood analysis system to execute the corresponding detection process, analyze and process the at least two types of optical signals detected by the sample detection device 50 in a real-time manner. In exemplary embodiments, the at least two types of optical signals may be processed by a Field-Programmable Gate Array (FPGA), a Digital Signal Processor (DSP) or CPU, and then automatically analyzed by the computer programs to acquire related data of platelets and/or platelet subpopulations.

As shown in FIG. 1, in the first exemplary implementation, the data analysis module 70 further includes a signal acquisition module 750, a classification and counting module 770 and an alarm module 790. The signal acquisition module 750 is operatively connected with the sample detection device 50. The signal acquisition module 750 may respectively acquire the electrical impedance signals of the first test sample and the forward scattered light signals and the fluorescent signals of the second test sample. The classification and counting module 770 is connected to the signal acquisition module 750. The classification and counting module 770 acquires first platelet detection data of the blood sample based on the electrical impedance signals. The classification and counting module 770 generates a scattergram of the second test sample based on the at least two types of optical signals, differentiates a white blood cell region from a platelet region in the scattergram, and then acquires second platelet detection data of the blood sample based on the platelet region in the scattergram. It should be noted that the scattergram herein may be presented not only in a graphical form, but also in a data array form, for example, in a numeric form of a table or a list with the same or similar resolution as the scattergram or histogram, or may be presented in any other appropriate manner known in the art. The alarm module 790 is connected to the classification and counting module 770. The alarm module 790 acquires an evaluation result based on a difference between the first platelet detection data and the second platelet detection data. The alarm module 790 determines whether the evaluation result meets a preset condition, and the alarm module 790 provides an alarm for indicating that the first platelet detection is abnormal and/or the impedance detection is abnormal when the determination result is yes, namely when the evaluation result meets the preset condition. The steps of specific methods executed by the classification and counting module 770 and the alarm module 790 will be described in detail later.

The user interface 90 is a medium for interaction and information exchange between the blood analysis system and users. The user interface 90 may display blood analysis data acquired by the classification and counting module 770 and/or an alarming signal for an abnormality acquired by the alarm module 790 to the users of the blood analysis system. In an embodiment, the user interface 90 may be a touch screen, which can identify touch control operations from users and display detection results. In another embodiment, the user interface 90 may include an input device and an output device. The input device may be a data input medium that is electrically connected to the data analysis module 70, such as a keyboard, a mouse and a microphone, etc. The output device may be a display screen, a printer, a speaker, an indicator light, etc. It can be understood that, when the alarm module 790 provides an alarm for an abnormality, the user interface may prompt users that the first platelet detection of the blood sample is abnormal and/or the electrical impedance detection of the sample analyzer is abnormal, by differentially marking the blood sample with colors, fonts or labels in a detection report or a displayed detection image, or by flashing, sound or other manners.

An alarm method provided by a second exemplary implementation of the present disclosure will be further described below with reference to the function modules of the blood analysis system described in the first exemplary implementation. The alarm method may be used automated blood analyzers, or may also be used in blood analysis systems provided with a flow cytometer and an electrical impedance detector. The alarm method may be executed by a processor in the form of computer programs. The computer programs may be provided in the automated blood analyzers, or may be independently provided in a computer that can directly or indirectly acquire blood cell detection signal data.

Figure 3:
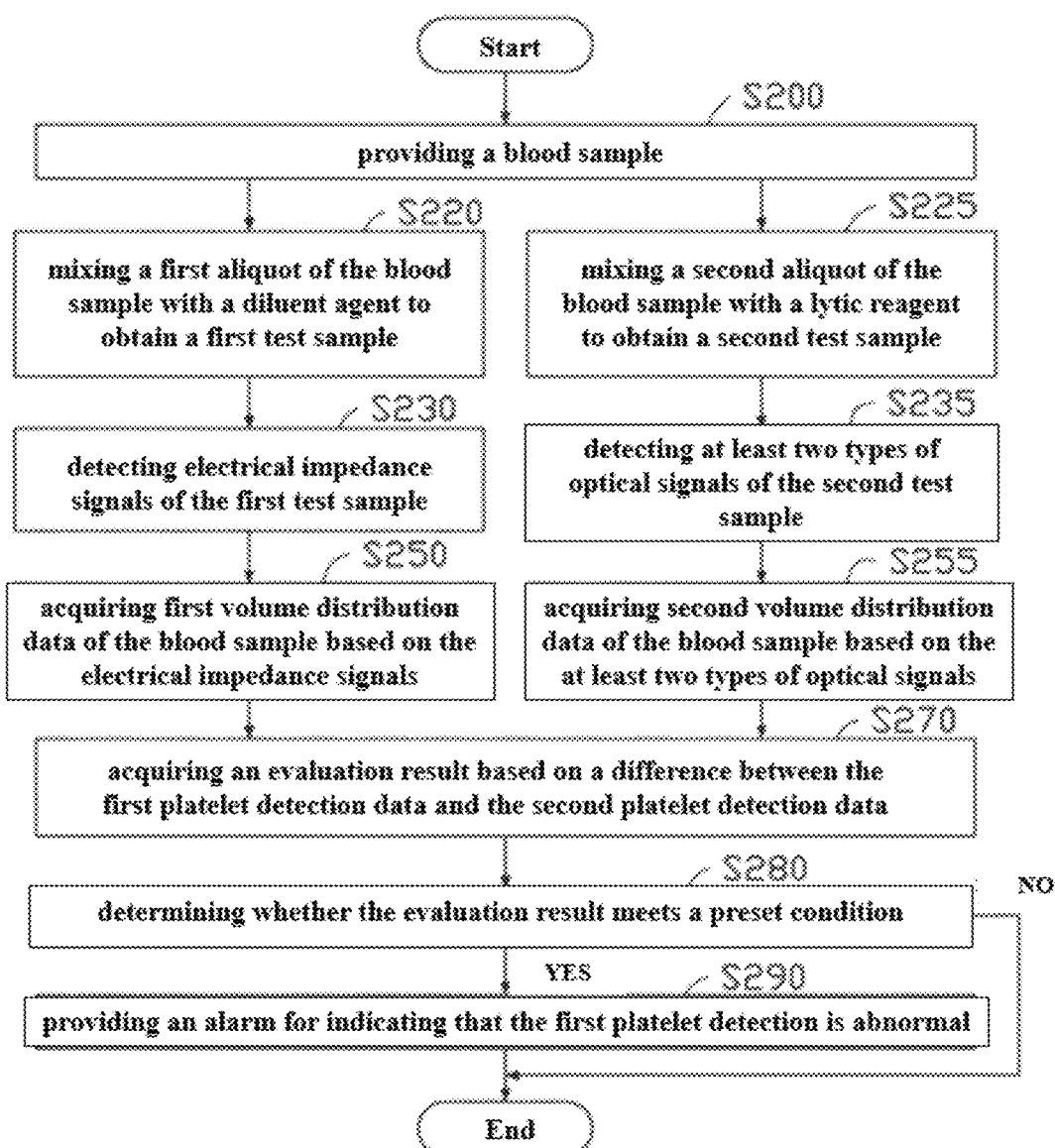
FIG. 3 is a flowchart of an alarm method provided by the present disclosure.

Please refer to the flowchart shown in FIG. 3. In the second exemplary implementation, the alarm method for providing an alarm for indicating that an abnormality is present in the sample analyzer includes the following steps:

Step S200: providing a blood sample.

Step S220: mixing a first aliquot of the blood sample with a diluent agent to obtain a first test sample for first platelet detection.

Step S225: mixing a second aliquot of the blood sample with a lytic reagent to obtain a second test sample for second platelet detection, wherein the lytic reagent includes a hemolytic agent for lysing red blood cells and a fluorescence dye for staining blood cells.

Step S230: detecting electrical impedance signals of the first test sample.

Step S235: detecting at least two types of optical signals of the second test sample, wherein the at least two types of optical signals include forward scattered light signals and fluorescent signals.

Step S250: acquiring first platelet detection data of the blood sample based on the electrical impedance signals acquired at step S230.

Step S255: acquiring second platelet detection data of the blood sample based on the at least two types of optical signals acquired at step S235.

Step S270: acquiring an evaluation result based on a difference between the first platelet detection data and the second platelet detection data.

Step S280: determining whether the evaluation result meets a preset condition. When the determination result is yes, step S290 is executed to provide an alarm for indicating that the first platelet detection is abnormal and/or the electrical impedance signal detection is abnormal. When the determination result is no, the process ends.

In a specific implementation, when the processor executes step S200, the sample collection unit 10 supplies the blood sample to the blood analysis system or the blood analyzer. When the processor executes steps S220 and S225, the sample treatment device 30 respectively prepares the first test sample and the second test sample. Reagents and preparation conditions for preparing the first test sample and the second test sample have been described in detail above, which will not be repeated herein. When the processor executes step S230, the electrical impedance detection unit 51 of the sample detection device 50 detects the electrical impedance signals of the first test sample; when the processor executes step S235, the optical detection unit 53 of the sample detection device 50 detects the at least two types of optical signals of the second test sample. When the processor executes steps S250 and S255, the data analysis module 70 respectively acquires the first and second platelet detection data. When the processor further executes steps S270-S290, the alarm module 790 of the data analysis module 70 determines whether the platelet detection is abnormal based on the first and second platelet detection data, and provides an alarm for the abnormality. It can be understood that, in the flow of the steps for alarming an abnormality, steps S220, S230 and S250 for acquiring the first platelet detection data and steps S225, S235 and S255 for acquiring the second platelet detection data may be executed in parallel or in sequence.

At step S250, those skilled in the art should understand that, an electrical impedance volume histogram of platelets and red blood cells in the first test sample may be generated based on the electrical impedance signals acquired at step S230. Generally, in the electrical impedance volume histogram, volumes of blood cells are measured in femtoliter (fL). A distribution curve of platelets can be differentiated from that of red blood cells in the volume histogram by one or more preset volume boundary values, and then characteristic parameters of platelets in the blood sample can be acquired based on the distribution curve of platelets. The one or more preset volume boundary values are empirical values or values that can be dynamically acquired based on empirical algorithm. In an embodiment, a volume range threshold for differentiating platelets may be 2-30 fL. The characteristic parameters of platelets include but not limited to platelet count (PLT), Mean Platelet Volume (MPV), Platelet Distribution Width (PDW). It should be noted that "first platelet detection data" herein includes volume distribution data of platelets and/or characteristic parameters reflecting volume distribution of platelets. The volume distribution data of platelets may be expressed in a numeric form, or in a graphical form.

At step S255, the present disclosure discloses a method for acquiring the second platelet detection data based on the at least two types of optical signals of the second test sample. In the first aspect of the present disclosure, red blood cells in the second test sample are lysed and blood cells in the second test sample are stained by the fluorescence dye, and the at least two types of optical signals include forward scattered light signals and fluorescent signals. Specifically, step S255 may include the following steps.

Step S2551: acquiring the at least two types of optical signals of the second test sample. Accordingly, for the blood analysis system in the first exemplary implementation, the signal acquisition module 750 acquires the at least two types of optical signals of the second test sample.

Step S2553: generating a scattergram of the second test sample based on the at least two types of optical signals. In an embodiment shown in FIG. 4A, an FL-FSC two-dimensional scattergram may be acquired based on intensities of the forward scattered light signals and the fluorescent signals of the second test sample. Accordingly, for the blood analysis system in the first exemplary implementation, the classification and counting module 770 generates the scattergram of the second test sample. In an alternative implementation, the at least two types of optical signals acquired at step S235 include forward scattered light signals, side scattered light signals and fluorescent signals, and the scattergram generated at step S2553 may also be an FSC-SSC scattergram, an FL-SSC scattergram, or a FL-FSC-SSC 3D scattergram. It can be understood that, when the at least two types of optical signals include other optical signals (such as medium-angle scattered light signals and fluorescent signals), the scattergram may also be 2D or 3D scattergram of other form. It can be understood that the abscissa and ordinate of the scattergram may also be other parameters of forward scattered light signals and side scattered light signals that reflect particle characteristics of the first test sample, and the abscissa and ordinate of the scattergram may also be nonlinear coordinate axis, such as logarithmic coordinate axis, to further highlight differences in distribution among particle populations.

Step S2555: differentiating a white blood cell region from a platelet region in the scattergram of the second test sample based on the at least two types of optical signals. Accordingly, for the blood analysis system in the first exemplary implementation, the classification and counting module 770 differentiates a white blood cell region from a platelet region in the scattergram of the second test sample based on the at least two types of optical signals. Taking the embodiment shown in FIG. 4A as an example, the white blood cell region W and the platelet region P can be differentiated from each other in the scattergram based on differences in intensities of the forward scattered light signals and the fluorescent signals of the second test sample. The white blood cell region W includes a region where white blood cells appear in the scattergram, and the platelet region P includes a region where platelets appear in the scattergram. Those skilled in the art should understand that the white blood cell region W and the platelet region P may be set by a gating technique.

Figure 4A:
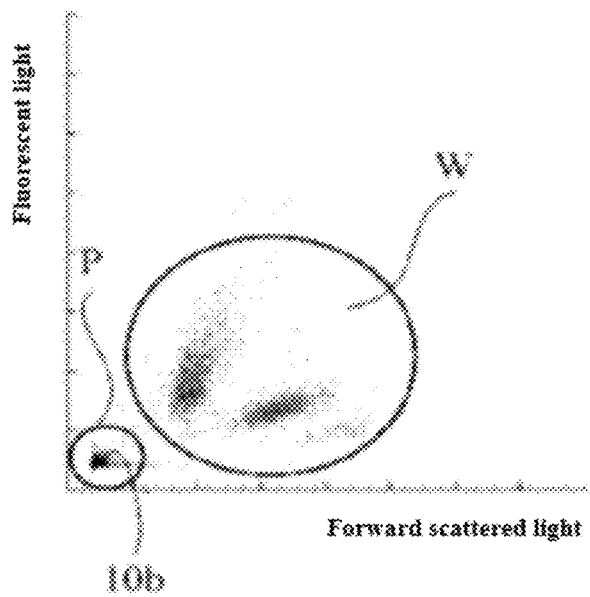
FIG. 4A is a scattergram generated by an embodiment of a second exemplary implementation of the present disclosure.

As shown in FIG. 4A, in the prior art, it is generally believed that in particle populations characterized by an optical scatter diagram of a hemolyzed blood sample, the particle population with relatively small scattered light intensities and fluorescence intensities mainly includes schistocytes and platelets. The inventors have found after repeated assumptions and experiments that, the lytic reagent may include one or more types of lytic agents for lysing red blood cells and a fluorescence dye for staining nucleated blood cells, platelets treated by the hemolytic agent are different in volume sizes and cellular contents from schistocytes and white blood cells, and a part of or all of platelets can be differentiated in the hemolyzed blood sample by an optical method (for example, by measuring scattered light signals and fluorescent signals).

Figure 4B:
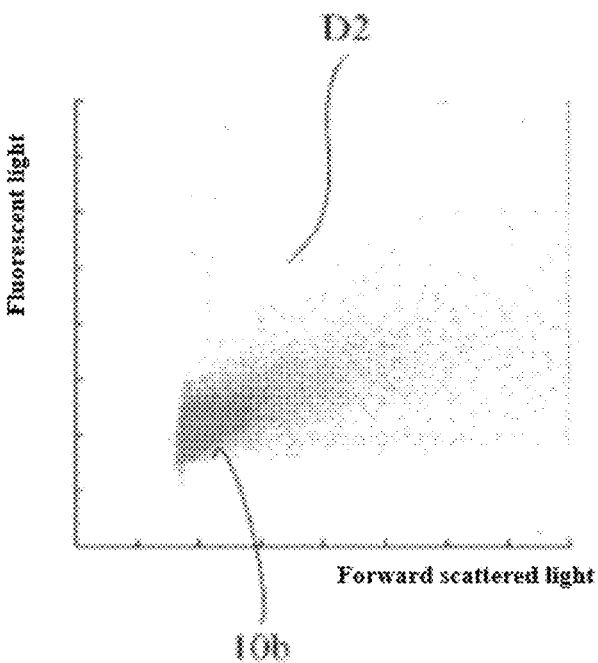
FIG. 4B is a partially enlarged view of a platelet region P in FIG. 4A.

In the second exemplary implementation, the platelet region P differentiated at step S2555 may include impurity particles such as schistocytes. As shown in FIG. 4A, the intensities of the forward scattered light signals of the platelet region P are substantially less than that of the white blood cell region W, and the intensities of the fluorescent signals of the platelet region P are substantially less than that of the white blood cell region W. FIG. 4B is a partially enlarged view of FIG. 4A, which is acquired by enlarging the platelet region P in the scattergram shown in FIG. 4A.

Step S2557: acquiring the second platelet detection data of the blood sample based on the platelet region P. Accordingly, for the blood analysis system in the first exemplary implementation, the classification and counting module 770 acquires the second platelet detection data of the blood sample based on the platelet region P.

In an implementation, at step S2557, the second platelet detection data of the test blood sample is calculated based on the forward scattered light signals of a particle population characterized in platelets $10b$.

In an embodiment, the volume (Vol) of each particle characterized in the platelets $10b$ may be calculated by using Equation (1):

$$Vol_a = \alpha * FSC \quad \text{Equation (1)}$$

wherein, FSC is the intensity of forward scattered light signal of each particle (also referred to as "individual event") characterized in the platelets 10b, and α is a constant.

In another embodiment, the volume (Vol) of each particle characterized in the platelets 10b may be calculated by using Equation (2):

$$Vol_b = \beta * \exp(\gamma * FSC) \quad \text{Equation (2)}$$

wherein, FSC is the intensity of forward scattered light signal of each individual event characterized in the platelets 10b, and β and γ are constants.

In another embodiment, the volume (Vol) of each particle characterized in the platelet 10b may be calculated by using Equation (3):

$$Vol_c = [1/(FSC * \sigma (2\pi)^{1/2})] \exp(-(\ln FSC - \mu)^2 / 2\sigma^2) \quad \text{Equation (3)}$$

where, FSC is the intensity of forward scattered light signal of each individual event characterized in the platelets 10b, and μ and σ are constants.

Figure 4C:
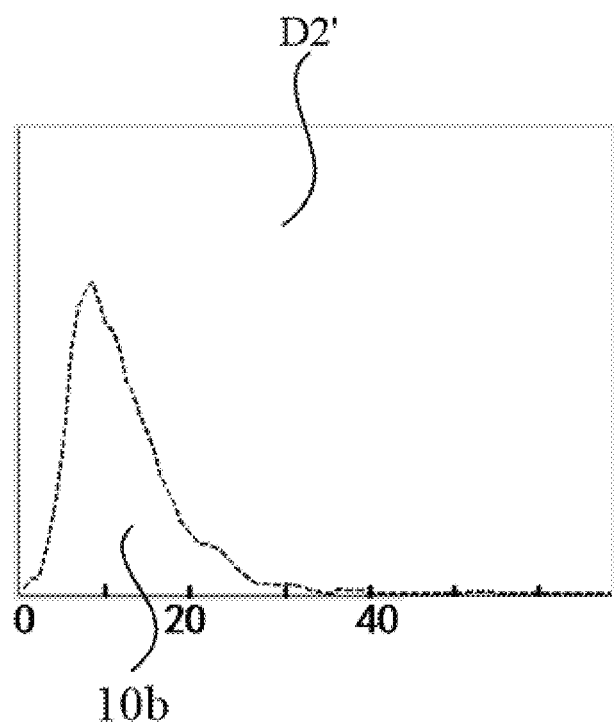
FIG. 4C is a derived volume histogram acquired based on the platelet region P in FIG. 4A.

At step S2557, volume distribution data corresponding to the platelets 10b may be acquired based on the volume (Vol) of each particle in the particle population characterized by the platelets 10b and a corresponding number of particles. Further, a volume distribution curve, which is referred to as a derived volume histogram herein, may be acquired based on the volume distribution data of the platelets 10b, as shown in FIG. 4C. Since the volume distribution data (or the derived volume histogram) of the platelets 10b contains information about platelets in the hemolyzed blood sample, the volume distribution data is considered as a form of the second platelet detection data herein.

Further, larger particles can be differentiated from smaller particles in the derived volume histogram by using a preset derived volume separation threshold, wherein the derived volume separation threshold may be selected from values between 10-20 fL, such as 10 fL, 12 fL, 15 fL or 20 fL. The inventors have found after repeated assumptions and experiments that the larger particles are mainly part of platelets with a relatively large volume in the test blood sample. Since the electrical impedance method cannot be used to differentiate among large platelets, schistocytes and microcytes with a similar volume, the abnormality of the first platelet detection data acquired by the electrical impedance detection method can be effectively alarmed by comparing a portion greater than the derived volume separation threshold in the derived volume histogram with that in the electrical impedance volume histogram acquired in the second exemplary implementation. Since the curve portion of the larger particles in the derived volume histogram separated by the derived volume separation threshold contains information about platelets in the hemolyzed blood sample, it is also considered as a form of the second platelet detection data herein. Alternatively, characteristic parameters such as an area of the curve portion may also be acquired based on the curve portion of the larger particles in the derived volume histogram, and the characteristic parameters are also a form of the second platelet detection data.

In an alternative implementation, the at least two types of optical signals acquired at step S235 include forward scattered light signals, side scattered light signals and fluorescent signals. Then, at step S2557, based on the forward scattered light signals and the side scattered light signals of the platelets 10b, the volume of each particle in the platelet region may also be calculated by using the Mie Scattering Theory (ZHANG Wei, LU Yuan, DU Shiming, et. al., Analysis on Mie Scattering Characteristics of Spherical Particles, Optical Technology, 2010-11: Volume 36 Issue 6: 936-939.), thereby acquiring volume distribution data of the particle population characterized by the platelets 10b, that is, the second platelet detection data. Alternatively, a derived volume histogram may be acquired based on the volume distribution data of the platelets 10b. Alternatively, a curve portion of larger particles in the derived volume histogram may be acquired based on the derived volume histogram and a derived volume separation threshold, and information of larger platelets in the test blood sample may be acquired based on the curve portion. Obviously, in the alternative implementation, the second platelet detection data may be acquired by using Equation (1), Equation (2) or Equation (3) based on the forward scattered light signals of the platelets 10b.

The second platelet detection data of the test blood sample may be acquired by sequentially executing steps S2551-S2557 in step S255. In the second exemplary implementation, at step S270, the evaluation result is acquired based on the difference between the first platelet detection data and the second platelet detection data. Accordingly, for the blood analysis system in the first exemplary implementation, the alarm module 790 acquires the evaluation result based on the difference between the first platelet detection data and the second platelet detection data. In order to acquire the evaluation result, step S270 may further include the following steps.

Step S2701: acquiring the first platelet detection data acquired at step S250 and the second platelet detection data acquired at step S255. It can be understood that in an implementation, presentation forms of the first and second platelet detection data which can be used for direct comparison may be selectively acquired at step S2701, for example, curve portions with volumes greater than a certain preset volume separation threshold in the electrical impedance volume histogram and the derived volume histogram, or, integral areas of the curve portions relative to abscissa "volume". It can be understood that, in another implementation, the first and second platelet detection data in other presentation forms may also be acquired at step S2701, for example, a half-peak width or a half-peak amplitude, and then after step S2701, at step S2703, the presentation forms of the first and second platelet detection data are matched, and the presentation forms of the platelet detection data which cannot be directly compared may be calculated and converted for comparison.

Step S2705: acquiring the evaluation result based on the presentation forms of the first and second platelet detection data for direct comparison. The evaluation result may be a result acquired by comparing numerical magnitudes and/or graphic differences between the first platelet detection data and the second platelet detection data. For the platelet detection data in a numerical form, at step S2705, an evaluation value reflecting the difference degree between the first platelet detection data and the second platelet detection data may be acquired by calculating the two by a mathematical expression, and then the evaluation value is compared with a preset threshold to acquire the evaluation result that the evaluation value is greater than, equal to, or less than the preset threshold. For the platelet detection data in a graphic form (such as histogram), the evaluation result acquired at step S2705 may be a preset qualitative description of the difference degree between the curves of the first platelet detection data and the second platelet detection data, such as "substantially similar" or "significantly different". It can be understood that, contents of the evaluation result may include one or more analysis and comparison results, for example, may include a plurality of numerical evaluation results of characteristic parameters that reflects information about platelets in the blood sample.

It should be noted that the evaluation value may be a difference degree of the second platelet detection data relative to the first platelet detection data, or a difference degree of the first platelet detection data relative to the second platelet detection data. It should be noted that methods for calculating the evaluation value is not limited to that disclosed herein. It can be understood that, the preset threshold described at step S2705 is set according to a setting mode of the evaluation value. Taking that the platelet detection data is an integral area value within a certain volume range in the volume histogram as an example, the evaluation value (EV) may be a difference, an absolute difference or a quotient between the second platelet detection data (PLT2) and the first platelet detection data (PLT1), or may also be a reciprocal, a multiple or an exponent of the difference, the absolute difference or the quotient. In an embodiment, EV=a*(PLT2/PLT1), where a is a preset coefficient. In another embodiment, EV=a*(PLT1/PLT2), where a is a preset coefficient. In another embodiment, EV=(PLT1−PLT2)b, where b is a preset coefficient. The evaluation value (EV) may also be other values that can reflect the difference between PLT1 and PLT2, for example, EV=(PLT1−PLT2)/PLT1, EV=(PLT1−PLT2)/PLT2, etc.

In the second exemplary implementation, at step S280, whether the evaluation result acquired at step S270 meets the preset condition is determined. When the determination result is yes, step S290 is executed to provide an alarm for indicating that the first platelet detection is abnormal and/or the electrical impedance signal detection process is abnormal. When the determination result is no, the process ends. Accordingly, for the blood analysis system in the first exemplary implementation, the alarm module 790 determines whether the evaluation result meets the preset condition: when the determination result is yes, namely the evaluation result meets the preset condition, outputs an alarm for indicating that the first platelet detection is abnormal and/or the electrical impedance signal detection process is abnormal; when the determination result is no, ends the process. Information of the alarm for indicating that the first platelet detection is abnormal and/or the electrical impedance signal detection process is abnormal acquired by the alarm module 790 may be transmitted to the user interface 90.

Figure 5A:
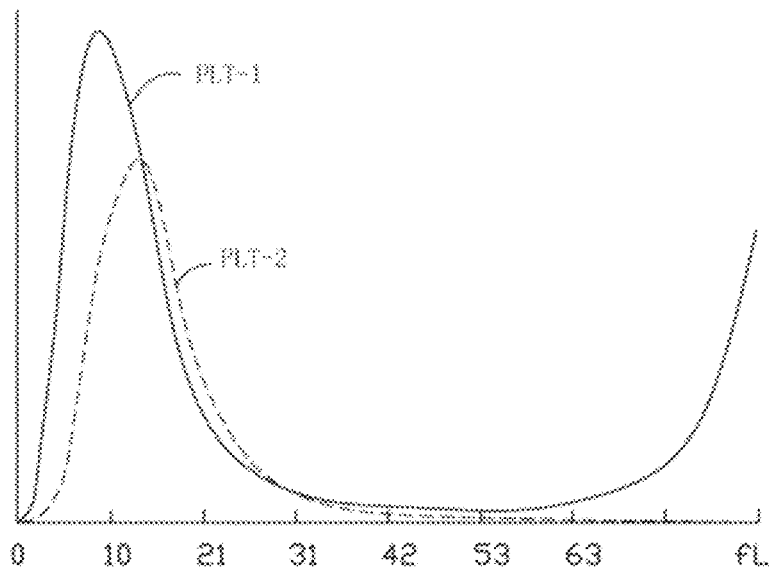
FIG. 5A is a schematic diagram for illustrating comparison between first and second platelet detection data under normal detection.
Figure 5B:
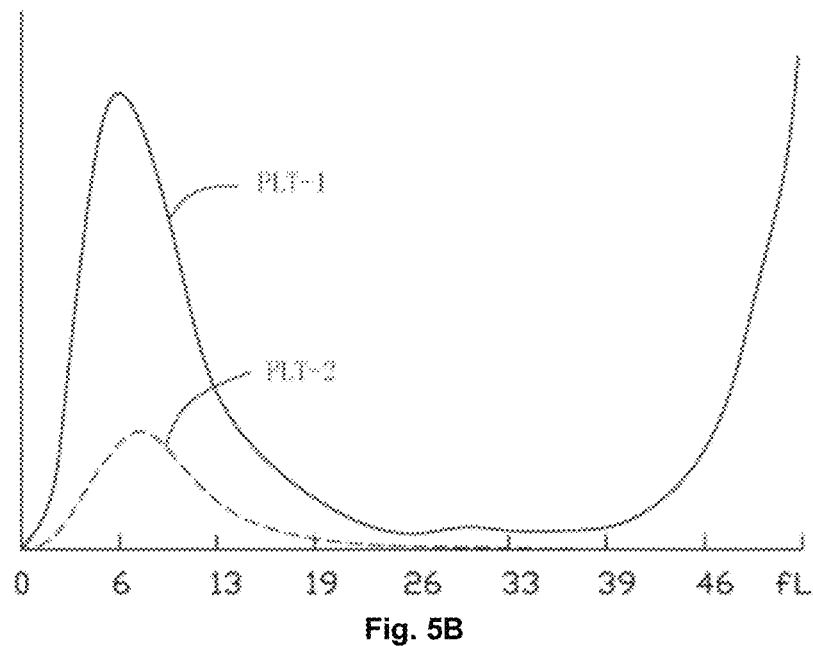
FIG. 5B is a schematic diagram for illustrating comparison between first and second platelet detection data under abnormal detection.

It can be understood that, under a normal condition (FIG. 5A), the difference between the first platelet detection data acquired by the electrical impedance method and the second platelet detection data acquired by the optical method described in the present disclosure is relatively small, that is, the evaluation result acquired by the systems and methods provided by the present disclosure includes information that the difference between the first and second platelet detection data is relatively small, and when the preset condition is that the first and second platelet detection data are significantly different, the determination result at step S280 is no, the process ends. Under an abnormal condition (FIG. 5B), such as an abnormal blood sample containing microcytes or an abnormality present in the electrical impedance detection channel, there may be a significant difference between the first and second platelet detection data, and when the preset condition is that the first and second platelet detection data are significantly different, the determination result at step S280 is yes, the abnormality of the first platelet detection and/or the abnormality of the impedance channel signal detection process are alarmed.

Specifically, when the evaluation result acquired at step S270 is a magnitude relationship between the evaluation value and a preset threshold, the preset condition set at step S280 may be that the evaluation value is greater than the preset threshold. When the evaluation result acquired at step S270 is a difference degree between graphs of the first and second platelet detection data, the preset condition set at step S280 may be that the graphics of the first and second platelet detection data are significantly different. It can be understood that the preset condition may include a plurality of preset conditions. When the plurality of preset conditions is all met, the determination result at S280 is yes.

In the second exemplary implementation, alternatively, the step of outputting other detection results and/or intermediate results may further be included. The detection results include but not limited to the first platelet detection data acquired at step S250 and the second platelet detection data acquired at step S255. The intermediate results include but not limited to the scattergram acquired at step S255, the platelet region in the scattergram, the derived volume histogram, the curve portion of the larger particles separated by the derived volume separation threshold, and the evaluation value or evaluation result acquired at step S270, etc.

It should be noted that the abnormality described herein may be caused by an abnormality of the blood analyzer. The abnormality of the blood analyzer includes but not limited to: an abnormality of the electrical impedance detection unit, and an abnormality of the optical detection unit. In this application, since the probability of an abnormality of the optical detection unit is generally low, an abnormality of the electrical impedance detection unit can be prompted by comparing the first and second platelet detection data. Further, the first and second platelet detection data of a plurality of samples can be continuously recorded and compared; and through statistical analysis, only when the data of the plurality of samples are continuously inconsistent, an abnormality of the electrical impedance detection unit is promoted, thereby increasing accuracy of alarm.

Figure 11:
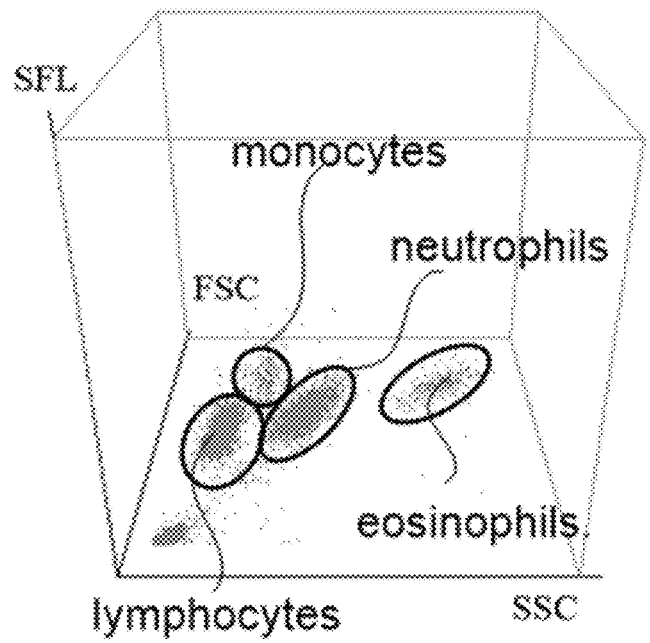
FIG. 11 is an SFL-SSC-FSC three-dimensional (3D) scattergram of second platelet detection according to an implementation of the present disclosure.
Figure 12:
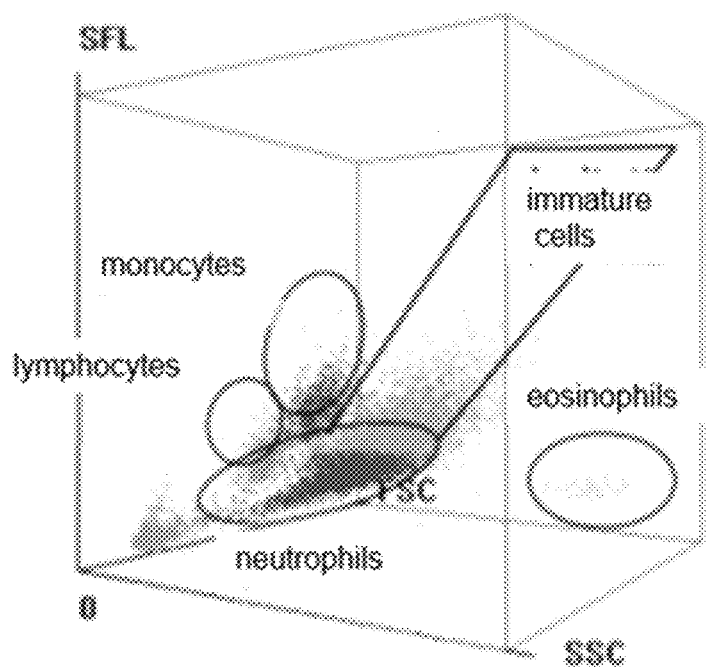
FIG. 12 is an FSC-SSC-SFL 3D scattergram of second platelet detection of a blood sample containing immature cells according to an implementation of the present disclosure.
Figure 13:
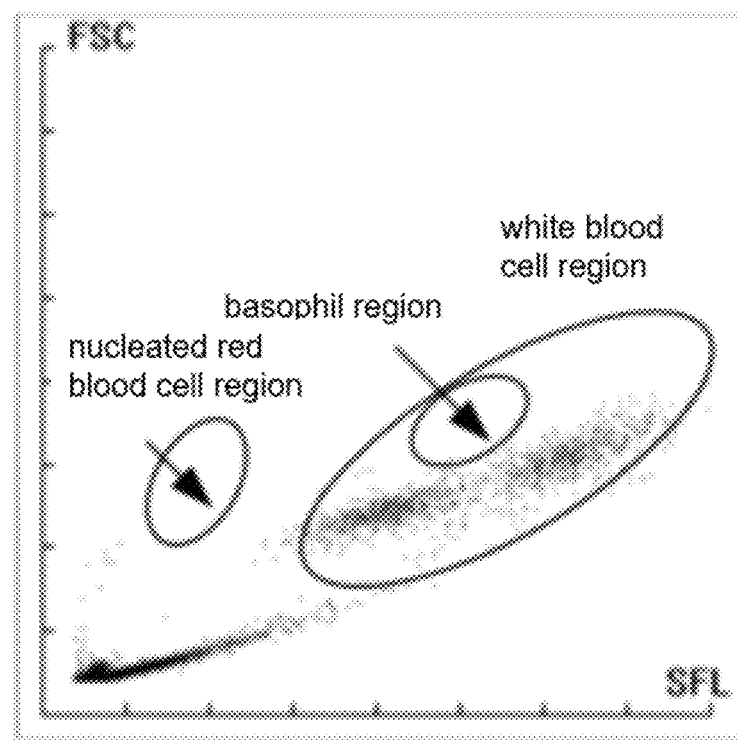
FIG. 13 is an FSC-SFL scattergram of second platelet detection of a blood sample containing nucleated red blood cells according to an implementation of the present disclosure.

In another embodiment, the second platelet detection may be performed by using white blood cell detection or nucleated red blood cell detection of an existing analyzer. That is, the second test sample may be a test solution for classifying or counting white blood cells or counting basophils or counting nucleated red blood cells. Since red blood cells in the test solution are lysed and blood cells are stained by a fluorescence dye, optical signals of each cell particle can also be acquired in optical detection. The inventors have found through researches that, in the scattergram acquired by the detection, there is also a platelet region P, which can be applied in aforementioned methods for alarming. At the same time, a white blood cell classification result can be acquired. As shown in FIG. 11, white blood cells are differentiated into four subpopulations: lymphocytes, monocytes, neutrophils and eosinophils based on the fluorescent signals, the side scattered light signals and the forward scattered light signals. Further, in other implementations, basophils are differentiated from other white blood cell subpopulations in the white blood cells based on the scattered light signals and the fluorescent signals. In other embodiments, the method may further include the steps of counting a number of white blood cells and reporting the count of white blood cells in the blood sample. Those skilled in the art should understand that, the method may further include the step of identifying nucleated red blood cells, immature cells or blast cells based on the scattered light signals and the fluorescent signals of the second test sample. For example, as shown in FIG. 12, when the blood sample contains immature cells, in the method, immature cells can be identified based on the scattered light signals and the fluorescent signals, and white blood cells can further be differentiated into four subpopulations: lymphocytes, monocytes, neutrophils and eosinophils. Or, for example, as shown in FIG. 13, nucleated red blood cells and white blood cells can be identified and counted based on the scattered lights and the fluorescent signals.

Figure 14:
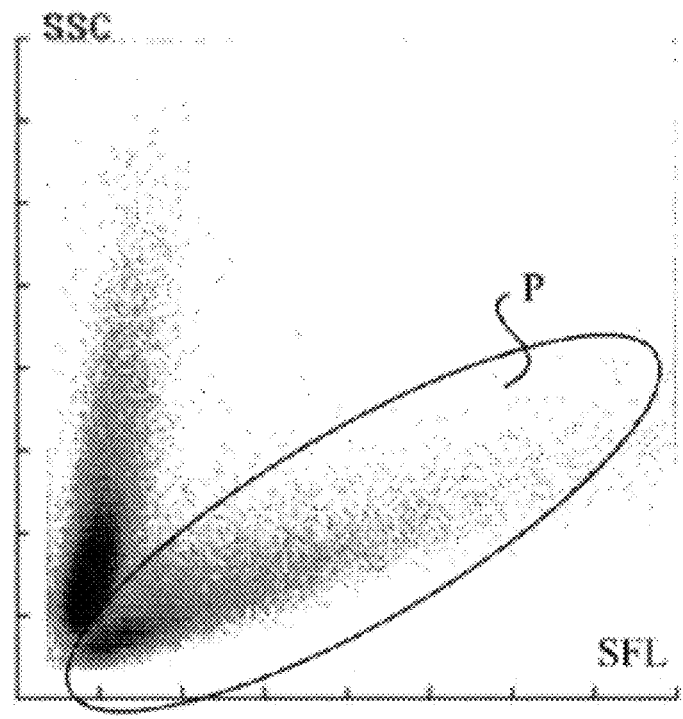
FIG. 14 is a platelet distribution region diagram corresponding to an SFL-SSC scattergram acquired by second platelet detection according to an implementation of the present disclosure.

It has been found through researches that the platelet region may also be differentiated by using a fluorescence-side scattered light (SFL-SSC) scattergram, as shown in FIG. 14. Therefore, when a sample passes through a nucleated red blood cell detection unit, fluorescent signals, forward scattered light signals and side scattered light signals are acquired at the same time, the P region can be differentiated by using a SFL-SSC scattergram, and then a derived platelet volume histogram is acquired at least based on the forward scattered light signal of each cell to obtained the second detection data.

A method for alarming an abnormality provided by a third exemplary implementation of the present disclosure will be described below. Compared with the method of the second exemplary implementation described above, in the third exemplary implementation, a different method for acquiring the second platelet detection data is adopted at step S255a. For the main analysis process and other steps of the third exemplary implementation, reference can be made to FIG. 3 and the contents described above, which will not be repeated herein.

In the third exemplary implementation, at step S225a, the second platelet detection data is acquired based on at least two types of optical signals of the second test sample, wherein the at least two types of optical signals include forward scattered light signals and fluorescent signals of the second test sample, red blood cells of which are lysed. Specifically, step S255a includes the following steps:

Step S2551a: acquiring the at least two types of optical signals of the second test sample.

Step S2553a: generating a scattergram of the second test sample based on the at least two types of optical signals.

Figure 6A:
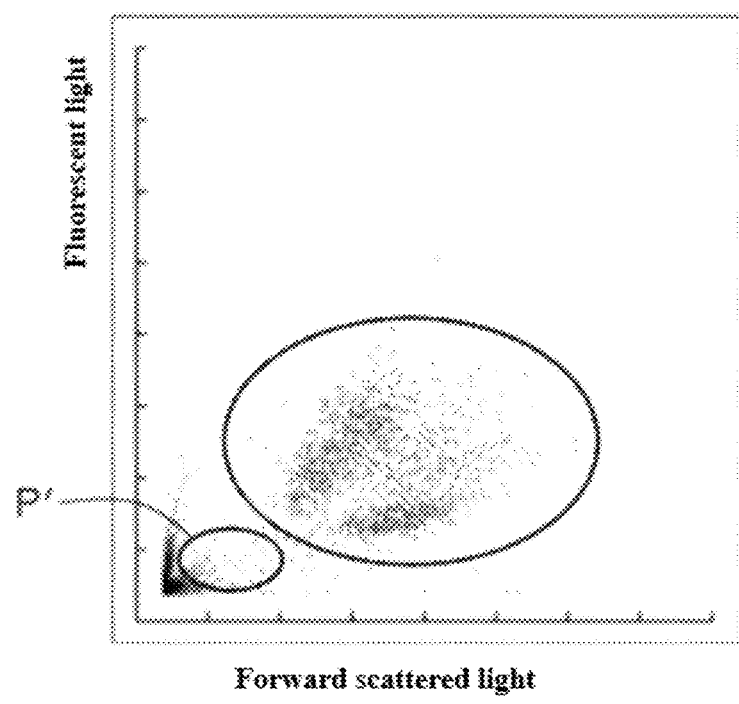
FIG. 6A is a scattergram generated by an embodiment of a third exemplary implementation of the present disclosure.

Step S2555a: differentiating a white blood cell region from a platelet region in the scattergram of the second test sample based on the at least two types of optical signals. In the third exemplary implementation, the platelet region differentiated at step S2555a is a large platelet region P', and the large platelet region P' is a region where large platelets in the second test sample appear in the scattergram. In an embodiment shown in FIG. 6A, the intensities of the forward scattered light signals of the large platelet region P' are substantially less than that of the white blood cell region W, and are substantially greater than that of schistocytes at the lower left corner of the scattergram. The intensities of the fluorescent signals of the large platelet region P' are substantially less than that of the white blood cell region W. A platelet derived volume histogram may also be acquired by using the foregoing method at least based on the large platelet region P', as shown in FIG. 6B. It should be noted that FIG. 6B is a schematic diagram. For the sake of easy understanding, the left part of the curve is fitted.

Step S2557a: acquiring the second platelet detection data of the blood sample based on the large platelet region P'. In the third exemplary implementation, the second platelet detection data may be large platelet detection data, such as volume distribution data of large platelets, a count of large platelets or other characteristic parameters that can reflect volume distribution of large platelets.

In an implementation, at step S2557a, the volume distribution data of large platelets may be acquired based on the forward scattered light signals of a particle population characterized in the large platelet region P'. Specifically, the forward scattered light signals may be converted into a volume of each particle in the large platelet region P' by using Equation (1), Equation (2) or Equation (3), thereby acquiring the volume distribution data of large platelets. In another implementation of the third exemplary implementation, the at least two types of optical signals acquired at step S235a include forward scattered light signals, side scattered light signals and fluorescent signals, and the volume of each particle in the large platelet region P' may also be calculated at step S2557a based on the forward scattered light signals and the side scattered light signals of the particle population characterized in the large platelet region P' by using the Mie Scattering Theory, thereby acquiring the volume distribution data of large platelets. Alternatively, a derived volume histogram of large platelets may be acquired based on the volume distribution data of large platelets.

Alternatively, a count value of large platelets may further be calculated based on the volume distribution data of large platelets. In the present disclosure, a volume threshold for defining large platelets may be set by users, and the volume threshold may be any numerical value between 10-20 fL, for example, large platelets may be platelets with a volume greater than 10 fL, 12 fL, 15 fL or 20 fL. Those skilled in the art should understand that the range of the large platelet region P' may be accordingly changed based on the set volume threshold of large platelets. Alternatively, characteristic parameters reflecting volume distribution of large platelets, such as count value of large platelets, volume distribution width of large platelets, may further be calculated based on the volume distribution data of large platelets.

In an implementation, a number of particles (or referred to as "event number") of the particle population characterized in the large platelet region P' may also be acquired at step S2557a, and a count value of large platelets is acquired based on the number of particles.

In the third exemplary implementation, at step S270a, the first platelet detection data acquired at step S250 and the second platelet detection data acquired at step S255a may be acquired, and an evaluation result is acquired based on a difference between the first platelet detection data and the second platelet detection data. It can be understood that the second platelet detection data used for step S270a may be the volume distribution data of large platelets (such as the derived volume histogram of large platelets), the count value of large platelets or other characteristic parameters reflecting volume distribution of large platelets. Accordingly, step S270a may include the step of pre-processing the first platelet detection data acquired at step S250, thereby making the forms of the acquired first and second platelet detection data matched to acquire the evaluation result based on the difference therebetween.

For other specific contents of the third exemplary implementation, reference can be made to the contents of the second exemplary implementation, which will not be repeated herein.

An alarm method provided by a fourth exemplary implementation of the present disclosure will be described below. Compared with the method mentioned in the second implementation for acquiring the second platelet detection data by using the platelet region, and the method mentioned in the third exemplary implementation for acquiring the second platelet detection data by using the large platelet region, in the fourth exemplary implementation, a different sample treatment method and a different data analysis method for acquiring the second platelet detection data is adopt at step S225b; specifically, the second platelet detection data includes information about platelets with various volumes in the second test sample, including a count value of platelets in the sample. For the main analysis process and other steps of the fourth exemplary implementation, reference can be made to FIG. 3 and the contents described above in the second exemplary implementation, which will not be repeated herein.

At step S225b, the lytic reagent for preparing the second test sample includes a hemolytic agent for lysing red blood cells and a fluorescence dye for staining blood cells. In the fourth exemplary implementation, by selection of the hemolytic agent and/or the fluorescence dye, optical differences between platelets and white blood cells and schistocytes in the hemolyzed second test sample are more significant, thereby realizing differentiation and counting of platelets.

Figure 7C:
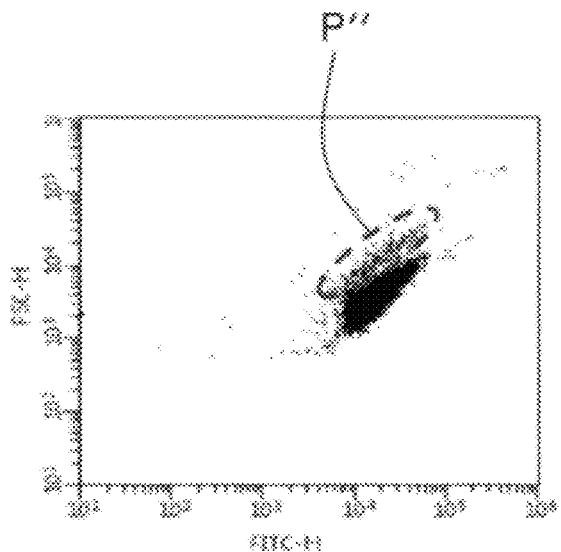
FIG. 7C is an FSC-FL scattergram of a second test sample stained by Rhodamine 123 dye.
Figure 7D:
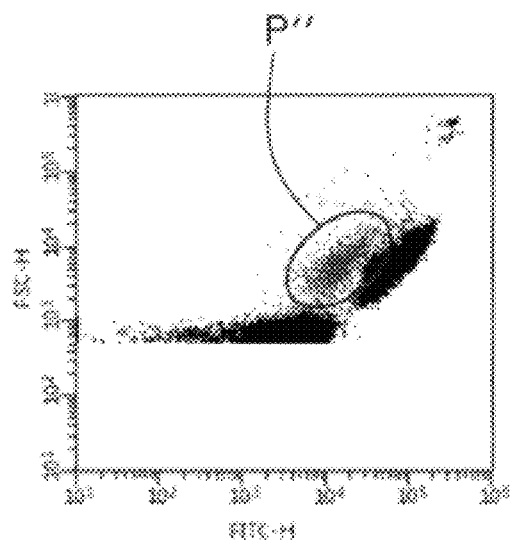
FIG. 7D is an FSC-FL scattergram of a second test sample stained by Mitotracker Deep Red dye.

In an implementation, at step S225b, blood cells in the blood sample are specifically stained by using a membrane dye or a mitochondrial dye, and the second test sample is prepared by lysing red blood cells using the hemolytic agent mentioned in the forgoing exemplary implementations, thereby differentiating platelets in the second test sample based on the at least two types of optical signals. The membrane dye may comprise Alexa Fluor series dyes, other commercially available membrane dyes, and variants using these dyes as parent. The mitochondrial dye may comprise Rhodamine 123 dyes, Mitotracker series dyes, other commercially available mitochondrial dyes, and variants using these dyes as parent. FIG. 7A shows an FSC-FL scattergram of a second test sample stained by Alexa Fluor 488 dye. FIG. 7B shows an FSC-FL scattergram of a second test sample stained by Mitotracker Red dye. FIG. 7C shows an FSC-FL scattergram of a second test sample stained by Rhodamine 123 dye. FIG. 7D shows an FSC-FL scattergram of a second test sample stained by Mitotracker Deep Red dye. It can be understood that, in order to further highlight differences among different particle populations, in this implementation, the coordinate axis of the scattergram generated at step S255b are logarithmic coordinate axis. As can be seen from FIGS. 7A-7D, by specific staining blood cells in blood sample using a membrane dye or a mitochondrial dye, a platelet region P''' can be differentiated in the scattergram. The platelet region P''' is a region where platelets in the second test sample appear in the scattergram.

In another implementation, at step S225b, red blood cells are lysed by using the hemolytic agent containing a glycoside compound disclosed in Chinese Invention Patent ZL200910109215.6, and the second test sample is prepared by adjusting dosage of the hemolytic agent for enhancing hemolysis intensity and staining blood cells using a nucleic acid dye, thereby differentiating platelets in the second test sample based on the at least two types of optical signals. All the contents disclosed in Chinese Invention Patent ZL200910109215.6 are incorporated herein by reference. The dye may be selected from the membrane dyes or the mitochondrial dyes described in the foregoing exemplary implementations, or may be selected from the fluorescence dyes mentioned in the foregoing patents, or from other fluorescence dyes suitable for staining white blood cells or reticulocytes, for example, fluorescence dye SYTO9.

In this implementation, the hemolytic agent includes a glycoside compound, a nonionic surfactant and an anionic organic compound.

The glycoside compound is selected from saponin and alkyl glycoside compounds. The glycoside compounds have the general formula R—(CH2)n-CH3, where n is an integer of 5-17, preferably, n is an integer of 6-14; R is a monosaccharide, a monosaccharide polymer or a polysaccharide. More specifically, R may be selected from commonly used carbohydrates, such as glucose, rhamnose, galactose, arabinose, xylose, maltose, mannose, ribose, lyxose, fucose, etc., and their deoxy sugar, and polymers thereof.

The nonionic surfactant has the general formula R1-R2-(CH2CH2O)n-H, where, R1 is a C8-C23 alkyl group or an alkenyl group. Preferably, R1 is a linear alkyl group, which is selected from octyl, decyl, lauryl, tetradecyl, hexadecyl and stearyl. Further preferably, R1 is a linear alkyl group, which is selected from lauryl, tetradecyl and hexadecyl. R2 is selected from —O—,

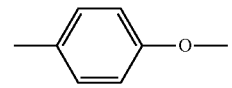

or —COO—, and n is an integer of 10-30.

The anionic organic compound is selected from anionic organic compounds of acids or salts with one or more hydroxy or sulfonic groups.

Figure 8A:
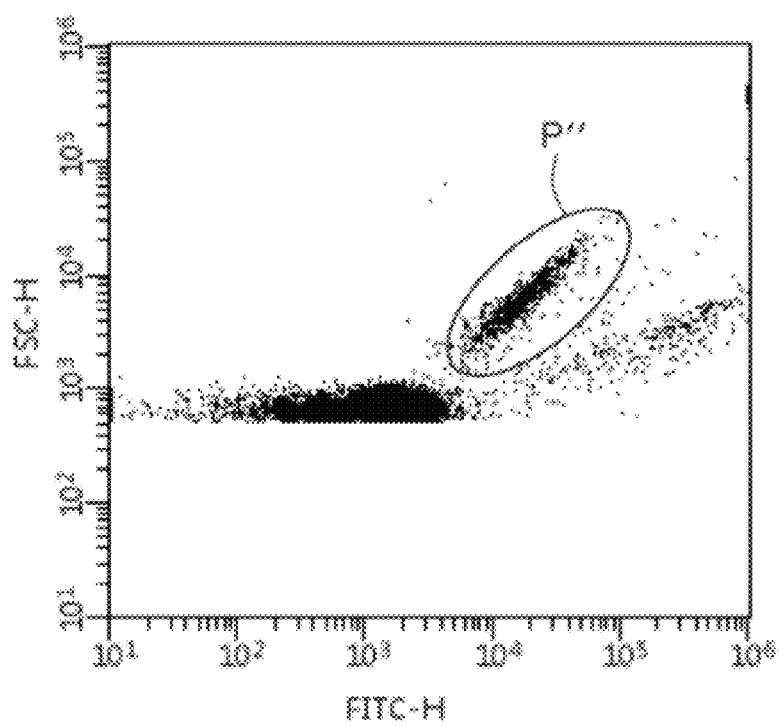
FIG. 8A is a scattergram of a second test sample acquired by an embodiment of a fourth exemplary implementation of the present disclosure.

FIG. 8A shows an FSC-SFL scattergram of a second test sample acquired by an embodiment of this implementation, wherein the lytic reagent used at step S225b includes a hemolytic agent and a nucleic acid dye described above. Specifically, in the embodiment shown in FIG. 8A, components and their concentrations of the lytic reagent are as follows:

| | |
|---|---|
| Fluorescence dye SYTO9 | 1.0 ppm |
| Saponin | 0.6 g/L |
| TRIS | 40 Mm |
| Sodium citrate | 5 g/L |
| Polyoxyethylene (23) Di-n-hexadecyl ether | 0.5 g/L |

The pH value of the lytic reagent is 7.5. 20 μL blood sample was added into 1 mL foregoing lytic reagent and incubated for 60 seconds at 45° C., and forward scattered light signals and 90-degree side fluorescent (SFL) signals were collected at an excitation wavelength of 488 nm. Based on the forward scattered light signals and the fluorescent signals, the scattergram shown in FIG. 8A can be acquired, and the platelet region P''' can further be differentiated in the scattergram. The platelet region P''' is a region where platelets in the second test sample appear in the scattergram. It can be understood that, in order to further highlight differences among different particle populations, in this implementation, coordinate axis of the scattergram generated at step S255b are logarithmic coordinate axis.

In other implementations, the above two implementations may also be used in combination. In other words, the lytic reagent used at step S225 includes a hemolytic agent and a fluorescence dye. The hemolytic agent includes a glycoside compound, a nonionic surfactant and an anionic organic compound. The fluorescence dye is selected from membrane dyes or mitochondrial dyes.

Please refer again to the flowchart of the method of the present disclosure shown in FIG. 3. As seen from the above, in the fourth exemplary implementation, at step S255b, the scattergram shown in FIG. 7A-7D or FIG. 8A may be generated based on the at least two types of optical signals, including the forward scattered light signals and the fluorescent signals. At step S255b, a white blood cell region and a platelet region P''' are differentiated from each other in the scattergram of the second test sample based on the at least two types of optical signals, and then the second platelet detection data of the blood sample is acquired based on the platelet region P'''.

In an implementation, volume distribution data of platelets may be acquired based on the forward scattered light signals of a particle population characterized in the platelet region P'''. Specifically, the forward scattered light signals may be converted into a volume of each particle in the platelet region P''' by using Equation (1), Equation (2) or Equation (3), thereby acquiring the volume distribution data of platelets. In another implementation, the at least two types of optical signals acquired at step S235b include forward scattered light signals, side scattered light signals and fluorescent signals, and the volume of each particle in the platelet region P''' may also be calculated at step S225b based on the forward scattered light signals and the side scattered light signals of the particle population characterized in the platelet region P''' by using the Mie Scattering Theory, thereby acquiring the volume distribution data of platelets. Alternatively, a derived volume histogram of platelets may be acquired based on the volume distribution data of platelets. Alternatively, characteristic parameters reflecting volume distribution of platelets further may be calculated based on the volume distribution data of platelets, such as a count value of platelets, a mean platelet volume and a volume distribution width. In another implementation, the count value of platelets may be acquired by acquiring a number of particles of the particle population characterized in the platelet region P'''.

It can be understood that the second platelet detection data acquired at step S255b may be the volume distribution data of platelets (such as the derived volume histogram of platelets), or may be the characteristic parameters reflecting volume distribution of platelets (such as the count value of platelets, the mean platelet volume and the volume distribution width, etc.).

Similarly, based on the first and second platelet detection data acquired at steps S250 and S255b, steps S270b-S290b are executed in succession to provide an alarm for abnormalities during the blood sample analysis process. For relevant specific contents reference can be made to the above, which will not be repeated herein. In this application, abnormality alarming includes: providing a prompt for indicating that the electrical impedance detection unit may be abnormal in the present sample detection or that the present detection result is unreliable due to the abnormality of the electrical impedance detection unit; or providing a prompt for indicating that the electrical impedance detection unit and/or the optical detection unit are/is abnormal in the present sample detection or that the present detection result is unreliable due to the abnormality.

Those skilled in the art should understand that all or part of the steps in the second, the third or the fourth exemplary implementation may be implemented by instructing related hardware of a blood analyzer through computer programs. The computer programs may be stored in a computer-readable storage medium and loaded into the blood analyzer having corresponding hardware system. When the computer programs are executed by a processor, the blood analyzer executes the analysis method for blood sample disclosed in the second, the third or the fourth exemplary implementation of the present disclosure.

The first aspect of the present disclosure further provides a blood analyzer. The blood analyzer includes a processor and a non-volatile computer-readable storage medium. The processor is configured to execute computer programs stored in the non-volatile computer-readable storage medium to implement the steps of the analysis method according to the second or the third or the fourth exemplary implementation.

The first aspect of the present disclosure further provides a non-volatile computer-readable storage medium storing computer programs thereon, wherein the computer programs, when executed by a processor, implement the steps of the analysis method of the second, the third or the fourth exemplary implementation. For the specific steps, reference can be made to various implementations and embodiments described above, which will not be repeated herein. Therefore, the analysis method of the second, the third or the fourth exemplary implementation may be implemented in the form of software function units and sold or used as an independent product.

The products and methods provided by the first aspect of the present disclosure can, based on the existing five-classification blood analysis system, respectively obtain detection data of platelets by using electrical impedance detection channel and white blood cell classification detection channel (for example, DIFF channel of BC-6800 blood analyzer produced by Shenzhen Mindray Bio-Medical Electronics Co., Ltd.), and provide an alarm for indicating an abnormal detection result by comparing the first and second platelet detection data acquired by the two detection channels. The products and methods provided by the first aspect of the present disclosure do not require a separate detection channel, and can provide users with more abundant detection information in a real-time manner, remind the users to perform a reexamination or recheck on abnormal platelet detection data, thereby increasing accuracy of platelet detection, without increasing the costs of the blood analysis system.

A second aspect of the present disclosure relates to a method, system and storage medium for providing an alarm for an abnormality of platelet detection and/or an abnormality of impedance channel by using electrical impedance signals and scattered light signals of a blood sample. Compared with the first aspect of the present disclosure, the second aspect of the present disclosure provides a product and method for providing an alarm for an abnormality of platelet detection and/or an abnormality of impedance detection channel, without using a fluorescence dye. It should be noted that in the second aspect of the present disclosure, a fluorescence dye may also be added to prepare a second test sample, and whether to use a fluorescence dye would not affect the realization of corresponding implementations.

A fifth exemplary implementation of the present disclosure provides an alarm method. Please refer again to the flowchart shown in FIG. 3. The alarm method includes the following steps:

Step S200: providing a blood sample.

Step S220: mixing a first aliquot of the blood sample with a diluent agent to obtain a first test sample for first platelet detection.

Step S225c: mixing a second aliquot of the blood sample with a lytic reagent to obtain a second test sample for second platelet detection, wherein the lytic reagent includes a hemolytic agent for lysing red blood cells.

Step S230: detecting electrical impedance signals of the first test sample.

Step S235c: detecting at least two types of optical signals of the second test sample. The at least two types of optical signals include first scattered light signals and second scattered light signals, wherein the first scattered light signals are forward scattered light signals, and the second scattered light signals are at least one type of medium-angle scattered light signals and side scattered light signals.

Step S250: are acquiring first platelet detection data of the blood sample based on the electrical impedance signals acquired at step S230.

Step S255c: acquiring second platelet detection data of the blood sample based on the at least two types of optical signals obtained at step S235.

Step S270c: acquiring an evaluation result based on a difference between the first platelet detection data and the second platelet detection data.

Step S280: determining whether the evaluation result meets a preset condition. When the determination result is yes, step S290 is executed to provide an alarm for indicating that the first platelet detection is abnormal and/or the electrical impedance signal detection is abnormal. When the determination result is no, the process ends.

Those skilled in the art should understand that all or part of the steps may be implemented by the blood analysis system shown as FIG. 1 through computer programs.

At step S225c, the second aliquot of the blood sample is mixed with the hemolytic agent to obtain the second test sample. The hemolytic agent may be any one of existing hemolysis reagents used by automated blood analyzers for classifying white blood cells, or may be any one of a cationic surfactant, a nonionic surfactant, an anionic surfactant and an amphiphilic surfactant or any combination thereof.

At step S235c, the forward scattered light signals, and at least one type of the medium-angle scattered light signals and the side scattered light signals of the second test sample may be acquired by one or more optical detectors. The medium-angle scattered light signals may be detected by an optical detector at an angle between forward scattered light and side scattered light. The medium-angle scattered light signals may be low medium-angle scattered light signals detected at an angle range from about 8° to about 24° relative to an incident beam, or high medium-angle scattered light signals detected at an angle range from about 25° to about 65° relative to the incident beam. As mentioned above, the forward scattered light signals may be detected at an angle range from about 1° to about 10° relative to the incident beam, preferably, the forward scattered light signals may be detected at an angle range from about 2° to about 6° relative to the incident beam. The side scattered light signals may be detected at an angle of about 90° relative to the incident beam, alternatively, the side scattered light signals may also be detected at an angle range from about 65° to about 115° relative to the incident beam.

Similar to the methods of the first aspect of the present disclosure, step S255c may include the following steps:

Step S2551c: acquiring the at least two types of optical signals of the second test sample, that is, the forward scattered light signals and at least one type of the medium-angle scattered light signals and the side scattered light signals.

Step S2553c: generating a scattergram of the second test sample based on the at least two types of optical signals.

Step S2555c: differentiating a white blood cell region from a platelet region in the scattergram acquired at step S2553c based on the at least two types of optical signals.

Step S2557c: acquiring the second platelet detection data of the blood sample based on the platelet region acquired at step S2555c.

In an implementation, similar to the second exemplary implementation described above, the platelet region P differentiated at step S2555c includes a region where the platelets appear in the scattergram, which may include a region where impurity particles like schistocytes appear in the scattergram. At step S2557c, the forward scattered light signals of a particle population characterized in the platelet region P are converted into a volume of each particle in the platelet region P by using Equation (1), Equation (2) or Equation (3), thereby acquiring volume distribution data of platelets. When the second scattered light signals are side scattered light signals, the volume of each particle in the platelet region P may also be calculated at step S2557c by using the Mie Scattering Theory based on the forward scattered light signals and the side scattered light signals of the particle population characterized in the platelet region P, thereby acquiring the volume distribution data of platelets. The volume distribution data may be represented in a numerical form or in a graphical form, such as a derived volume histogram.

Further, larger particles can be differentiated from smaller particles in the derived volume histogram by using a preset derived volume separation threshold. The derived volume separation threshold may be selected from values between 10-20 fL, such as 10 fL, 12 fL, 15 fL or 20 fL. In the separated derived volume histogram, a curve portion of the larger particles contains information about platelets in hemolyzed blood sample and may be regarded as a form of the second platelet detection data. Alternatively, characteristic parameters such as an area of the curve portion may also be acquired based on the curve portion of the larger particles in the derived volume histogram. The characteristic parameters may also be regarded as a form of the second platelet detection data.

Figure 9:
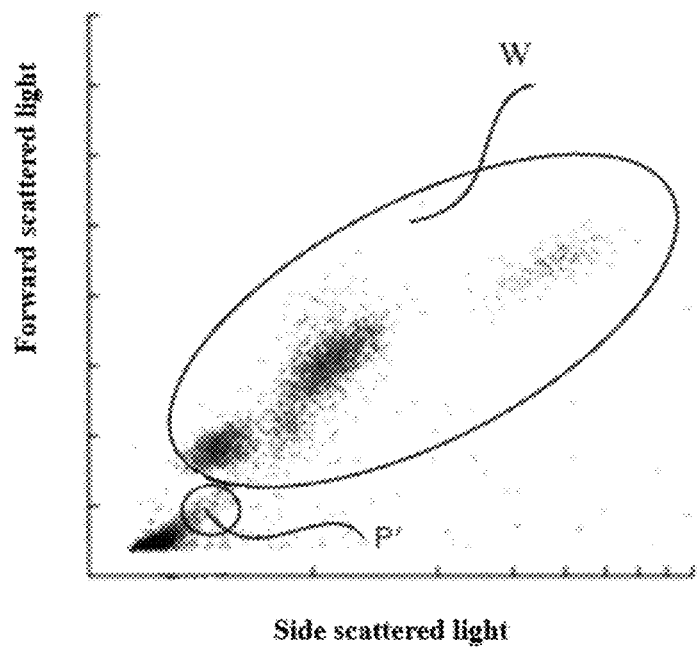
FIG. 9 is a schematic diagram for illustrating the differentiation of a platelet region in a scattergram according to an embodiment of the fifth exemplary implementation of the present disclosure.

In another implementation, similar to the third exemplary implementation described above, the platelet region differentiated at step S2555c is a large platelet region P', and the large platelet region P' is a region where large platelets in the second test sample appear in the scattergram. FIG. 9 shows an FSC-SSC scattergram generated by an embodiment of this implementation. At step S2557c, the scattered light signals of a particle population characterized in large platelet region P' may be converted into a volume of each particle in the large platelet region P' by using Equation (1), Equation (2), Equation (3) or Mie Scattering Theory, thereby acquiring volume distribution data of large platelets. Alternatively, a derived volume histogram of large platelets may be acquired based on the volume distribution data of large platelets. Alternatively, the characteristic parameters reflecting volume distribution of large platelets, such as a count value of large platelets, a volume distribution width of large platelets, may also be calculated based on the volume distribution data of large platelets. Alternatively, a count value of large platelets may also be acquired at step S2557c by acquiring a number of particles of the particle population characterized in the large platelet region P'. It can be understood that, in the implementation, the second platelet detection data may be the volume distribution data of large platelets (such as derived volume histogram of large platelets), the count value of large platelets or other characteristic parameters reflecting volume distribution of large platelets.

Figure 8B:
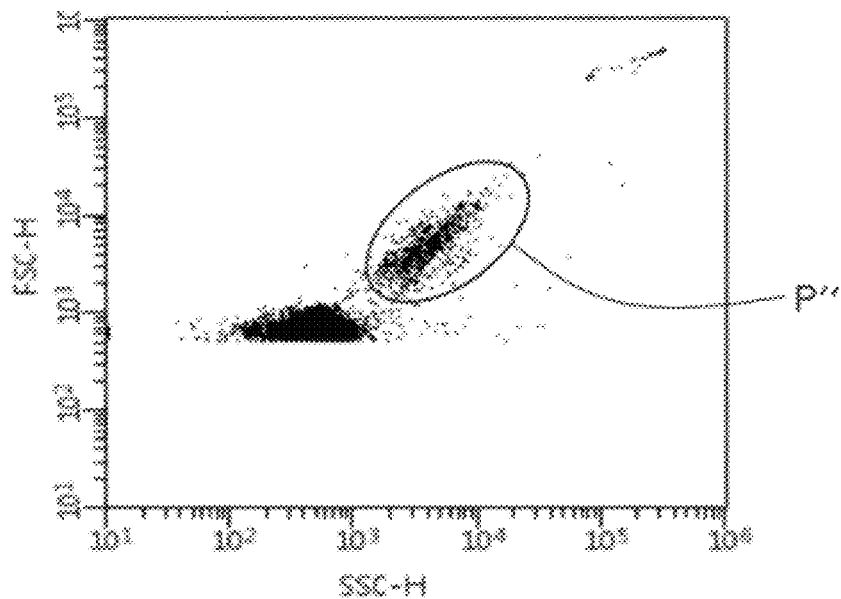
FIG. 8B is a scattergram of a second test sample acquired by an embodiment of a fifth exemplary implementation of the present disclosure.

In another implementation, similar to the fourth exemplary implementation mode described above, the platelet region differentiated at step S2555c is a platelet region P''', and the platelet region P''' is a region where platelets in the second test sample appear in the scattergram. In the implementation, at step S225c, the second test sample is prepared by using the hemolytic agent containing a glycoside compound disclosed in Chinese Invention Patent ZL200910109215.6, without using a nucleic acid dye. It has been found through researches that, by only increasing hemolysis intensity without using a dye, the platelet region P''' may appear in the scattergram based on the two types of scattered lights. FIG. 8B shows an FSC-SSC scattergram acquired by an embodiment of the implementation. At step S2557c, volume distribution data of platelets may be acquired based on the forward scattered light signals (or the forward scattered light signals and the side scattered light signals) of the particle population characterized in the platelet region P''', and a derived volume histogram of platelets and characteristic parameters reflecting volume distribution of platelets, such as a count value of the platelets, a mean platelet volume and a volume distribution width, may also be acquired based on the volume distribution data of platelets. At step S2557c, a count value of platelets may also be acquired by acquiring a number of particles of the particle population characterized in the platelet region P'''.

In the fifth exemplary implementation, the evaluation result is acquired at step S270c by analyzing the difference between the first platelet detection data acquired at step S250 and the second platelet detection data acquired at step S255c. At step S280, whether the evaluation result acquired at step S270c meets a preset condition is determined. When the determination result is yes, step S290 is executed to provide an alarm for indicating the first platelet detection is abnormal and/or the electrical impedance signal detection is abnormal. When the determination result is no, the process ends. For specific contents of steps S270c-290, reference can be made to the contents of the second, the third or the fourth exemplary implementation described above, which will not be repeated herein.

In the fifth exemplary implementation, alternatively, the step of outputting other detection results and/or intermediate results may further be included. The detection results include but not limited to the first platelet detection data acquired at step S250 and the second platelet detection data acquired at step S255c. The intermediate results include but not limited to the scattergram acquired at step S255c, the platelet region in the scattergram, the derived volume histogram, the curve portion of the larger particles separated by the derived volume separation threshold, and the evaluation value or the evaluation result acquired at step S270c, etc.

Further, in the above exemplary implementations, particularly in the fourth and the fifth exemplary implementations, a count value of platelets can be acquired. However, the probability of an abnormality of the optical detection unit is generally low, the count value of platelets acquired from the second platelet detection data can be outputted and reported to users in order to report the detection result of the test sample as soon as possible. That is, when the evaluation result is that there is no significant difference therebetween, the count value of platelets acquired from the first platelet detection data is outputted; when the evaluation result is that there is a significant difference therebetween, the count value of platelets acquired from the second platelet detection data is outputted. Preferably, the result can be marked to prompt the users that the result contains the count value of platelets acquired by the optical detection method under the hemolysis condition, so as to be differentiated from the count value of platelets acquired by the electrical impedance method.

Those skilled in the art should understand that all or part of the steps in the fifth exemplary implementation can be implemented by instructing related hardware of a blood analyzer through computer programs. The computer programs may be stored in a computer-readable storage medium and loaded into the blood analyzer having corresponding hardware system. When the computer programs are executed by a processor, the blood analyzer executes the analysis method for blood sample disclosed in the fifth exemplary embodiment of the present disclosure.

The second aspect of the present disclosure further provides a blood analyzer. The blood analyzer includes a processor and a non-volatile computer-readable storage medium. The processor is configured to execute computer programs stored in the non-volatile computer-readable storage medium to implement the steps of the analysis method of the fifth exemplary implementation.

The second aspect of the present disclosure further provides a non-volatile computer-readable storage medium storing computer programs thereon, wherein the computer programs, when executed by a processor, implement the steps of the analysis method of the fifth exemplary implementation. For the specific steps, reference can be made to various implementations and embodiments described above, which will not be repeated herein. Therefore, the analysis method of the fifth exemplary implementation may be implemented in the form of software function units and sold or used as an independent product.

Corresponding to the fifth exemplary implementation, the second aspect of the present disclosure further provides a blood analysis system. Please refer to FIG. 1 again, the blood analysis system includes a sample collection unit 10, a sample treatment device 30, a sample detection device 50, a data analysis module 70 and a user interface 90.

The sample treatment device 30 includes at least one mixing chamber, which is configured to mix a first aliquot of a blood sample with a diluent agent to obtain a first test sample, and mix a second aliquot of the blood sample with a lytic reagent to obtain a second test sample. The lytic reagent includes a hemolytic agent for lysing red blood cells.

The sample detection device 50 includes an electrical impedance detection unit 51 and an optical detection unit 53. The electrical impedance detection unit is configured to detect electrical impedance signals of the first test sample. The optical detection unit 53 is configured to detect at least two types of optical signals of the second test sample. The at least two types of optical signals include first scattered light signals and second scattered light signals, wherein the first scattered light signals are forward scattered light signals, and the second scattered light signals are at least one type of medium-angle scattered light signals and side scattered light signals.

The data analysis module 70 includes a signal acquisition module 750, a classification and counting module 770 and an alarm module 790. The signal acquisition module 750 acquires the electrical impedance signals of the first test sample and the at least two types of optical signals of the second test sample. The classification and counting module 770 acquires first platelet detection data of the blood sample based on the electrical impedance signals. The classification and counting module 770 generates a scattergram of the second test sample based on the at least two types of optical signals, differentiates a white blood cell region from a platelet region in the scattergram based on the at least two types of optical signals, and then acquires second platelet detection data of the blood sample based on the platelet region. The alarm module 790 acquires an evaluation result based on a difference between the first platelet detection data and the second platelet detection data, and then determines whether the evaluation result meets a preset condition. When the determination result is yes, an alarm for indicating that the platelet detection is abnormal and/or the impedance channel is abnormal is provided. When the determination result is no, the process ends.

For specific implementations of other specific structures and function modules of the blood analysis system, reference can be made to corresponding contents described above, which will not be repeated herein.

Compared with the products and methods provided by the first aspect of the present disclosure, the blood analysis system, analysis method, blood analyzer and storage medium provided by the second aspect can provide an alarm for indicating that the platelet detection is abnormal and/or the impedance detection is abnormal without using a fluorescence dye, and can provide users with more abundant detection information, and remind the users to perform a reexamination or recheck on the platelet detection results without increasing the costs of the blood analysis system and the costs of the reagents used in the blood analysis process, thereby increasing accuracy of platelet detection or discovering an abnormality in the sample analyzer in good time.

Figure 10:
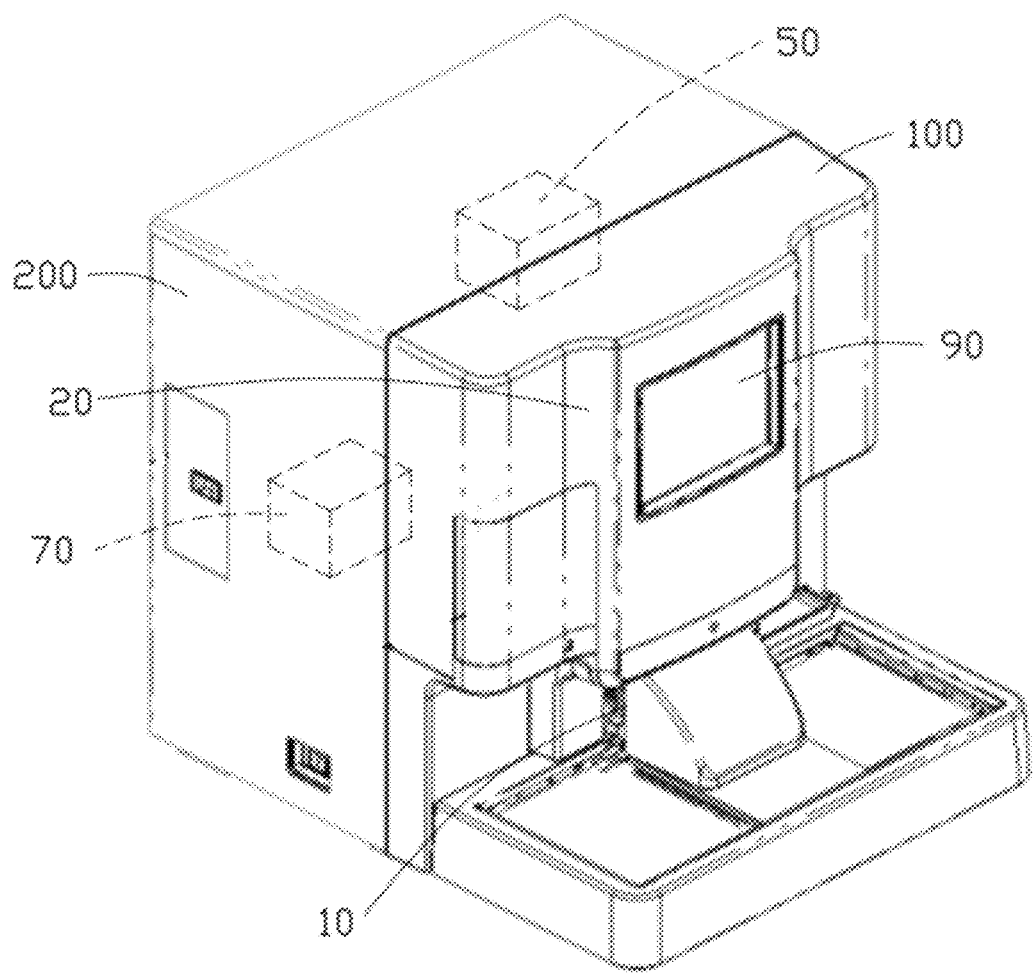
FIG. 10 is an overall stereoscopic diagram of a blood analysis system provided by the present disclosure.

FIG. 10 is an overall stereoscopic diagram of a blood analysis system provided the present disclosure. As shown in FIG. 10, the blood analysis system includes a first housing 100, a second housing 200, a sample collection unit 10, a sample treatment device 30, a sample detection device 50, a data analysis module 70 and a user interface 90. In the implementation, the sample detection device 50 and the data analysis module 70 are arranged inside the second housing 200, and are respectively arranged on both sides of the second housing 200. The sample treatment device 30 is arranged inside the first housing 100. The user interface 90 and the sample collection unit 10 are arranged on the outer surface of the first housing 100.

The above embodiments are the preferred implementations of the present disclosure, but the present disclosure is not limited to the above embodiments, and the above implementations are only for interpreting claims. Any changes or replacements that can be easily conceived by those skilled in the art within the technical scope disclosed in the present disclosure are included within the protection scope of the present disclosure.

What is claimed is:

1. An alarm method for providing an alarm for indicating that an abnormality is present in a sample analyzer, comprising:
providing a blood sample;
mixing a first aliquot of the blood sample with a diluent agent to prepare a first test sample for first platelet detection;
mixing a second aliquot of the blood sample with a lytic reagent to prepare a second test sample for second platelet detection, wherein red blood cells in the second test sample are lysed;
detecting electrical impedance signals of the first test sample;
detecting at least two types of optical signals of the second test sample;
acquiring first platelet detection data of the blood sample based on the electrical impedance signals;
acquiring second platelet detection data of the blood sample based on the at least two types of optical signals, wherein the first platelet detection data and the second platelet detection data comprise a same type of data selected from at least one of: a platelet count, a mean platelet volume, a platelet volume distribution width, or a platelet volume histogram, wherein acquiring second platelet detection data of the blood sample based on the at least two types of optical signals comprises:
generating a scattergram of the second test sample based on the at least two types of optical signals;
differentiating a white blood cell region from a platelet region in the scattergram based on the at least two types of optical signals; and
acquiring the second platelet detection data of the blood sample based on the platelet region;
calculating an evaluation value reflecting a difference degree between the first platelet detection data and the second platelet detection data;
comparing the evaluation value with a preset threshold; and
providing an alarm for indicating that an abnormality is present in the first platelet detection and/or an abnormality is present in the step of electrical impedance signal detection of the sample analyzer, when the evaluation value is greater than the preset threshold,
wherein the lytic reagent comprises a hemolytic agent for lysing red blood cells and a fluorescent dye for staining blood cells, and the at least two types of optical signals comprise forward scattered light signals and fluorescent signals; or wherein the lytic reagent comprises a hemolytic agent for lysing red blood cells, and the at least two types of optical signals comprise first scattered light signals and second scattered light signals, wherein the first scattered light signals are forward scattered light signals, and the second scattered light signal are at least one type of medium-angle scattered light signals and side scattered light signals.

2. The alarm method according to claim 1, comprising: outputting a prompt that the abnormality of the first platelet detection is caused by the abnormality in the step of the electrical impedance signal detection and/or that the first platelet detection data is unreliable.

3. The alarm method according to claim 1, wherein acquiring the second platelet detection data of the blood sample based on the platelet region comprises:
acquiring a derived platelet volume histogram based on the forward scattered light signals of a particle population in the platelet region; or
acquiring the second platelet detection data of the blood sample based on a number of particles in the platelet region.

4. The alarm method according to claim 1, wherein the at least two types of optical signals comprise forward scattered light signals and fluorescent signals of the second test sample, and acquiring the second platelet detection data of the blood sample based on the at least two types of optical signals comprises:
generating the scattergram of the second test sample based on the forward scattered light signals and the fluorescent signals of the second test sample;
differentiating the white blood cell region from a large platelet region of the platelet region in the scattergram based on the forward scattered light signals and the fluorescent signals of the second test sample; and
acquiring the second platelet detection data of the blood sample based on the large platelet region.

5. The alarm method according to claim 1, wherein the lytic reagent comprises a hemolytic agent for lysing red blood cells and a fluorescence dye for staining blood cells, and the two types of optical signals comprise scattered light signals and fluorescent signals, and the method further comprises classifying white blood cells into white blood cell subpopulations, or counting white blood cells or identifying nucleated red blood cells or immature cells or basophils according to the scattered light signals and the fluorescent signals; or the lytic reagent comprises a hemolytic agent for lysing red blood cells, and the two types of optical signals comprise first scattered light signals and second scattered light signals, wherein the first scattered light signals are forward scattered light signals, and the second scattered light signals are at least one type of medium-angle scattered light signals and side scattered light signals, and the method further comprises classifying white blood cells into white blood cell subpopulations or identifying basophils according to the first scattered light signals and the second scattered light signals.

6. The alarm method according to claim 1, further comprising the following steps:

outputting the first platelet detection data if there is no alarm for abnormality; and outputting the second platelet detection data if there is an alarm for abnormality.

7. The alarm method according to claim 1, comprising: continuously recording and counting comparison results of evaluation values of platelet detection for a plurality of blood samples, and providing an alarm for indicating that an abnormality is present in the electrical impedance signal detection when the continuous comparison results of the plurality of blood samples indicating the evaluation values being greater than the preset threshold.

8. A non-transitory computer-readable storage medium with a computer program stored thereon, wherein the computer program, when executed by a processor, implements the following steps:

detecting electrical impedance signals of a first test sample, wherein the first test sample is prepared by mixing a first aliquot of a blood sample with a diluent agent for first platelet detection;

detecting at least two types of optical signals of a second test sample, wherein the second test sample is prepared by mixing a second aliquot of the blood sample with a lytic reagent for second platelet detection, wherein red blood cells in the second test sample are lysed;

acquiring first platelet detection data of the blood sample based on the electrical impedance signals;

acquiring second platelet detection data of the blood sample based on the at least two types of optical signals, wherein the first platelet detection data and the second platelet detection data comprise a same type of data selected from at least one of: a platelet count, a mean platelet volume, a platelet volume distribution width, or a platelet volume histogram, wherein acquiring second platelet detection data of the blood sample based on the at least two types of optical signals comprises:

generating a scattergram of the second test sample based on the at least two types of optical signals;

differentiating a white blood cell region from a platelet region in the scattergram based on the at least two types of optical signals; and acquiring the second platelet detection data of the blood sample based on the platelet region;

calculating an evaluation value reflecting a difference degree between the first platelet detection data and the second platelet detection data;

comparing the evaluation value with a preset threshold; and providing an alarm for indicating that an abnormality is present in the first platelet detection and/or an abnormality is present in the step of electrical impedance signal detection of a sample analyzer, when the evaluation value is greater than the preset threshold, wherein the lytic reagent comprises a hemolytic agent for lysing red blood cells and a fluorescent dye for staining blood cells, and the at least two types of optical signals comprise forward scattered light signals and fluorescent signals; or wherein the lytic reagent comprises a hemolytic agent for lysing red blood cells, and the at least two types of optical signals comprise first scattered light signals and second scattered light signals, wherein the first scattered light signals are forward scattered light signals, and the second scattered light signal are at least one type of medium-angle scattered light signals and side scattered light signals.

9. The non-transitory computer-readable storage medium according to claim 8, the steps comprising: outputting a prompt that the abnormality of the first platelet detection is caused by the abnormality in the step of the electrical impedance signal detection and/or that the first platelet detection data is unreliable.

10. The non-transitory computer-readable storage medium according to claim 8, wherein acquiring the second platelet detection data of the blood sample based on the platelet region comprises:

acquiring a derived platelet volume histogram based on the forward scattered light signals of a particle population in the platelet region; or acquiring the second platelet detection data of the blood sample based on a number of particles in the platelet region.

11. The non-transitory computer-readable storage medium according to claim 8, wherein the at least two types of optical signals comprise forward scattered light signals and fluorescent signals of the second test sample, and acquiring the second platelet detection data of the blood sample based on the at least two types of optical signals comprises:

generating the scattergram of the second test sample based on the forward scattered light signals and the fluorescent signals of the second test sample;

differentiating the white blood cell region from a large platelet region of the platelet region in the scattergram based on the forward scattered light signals and the fluorescent signals of the second test sample; and acquiring the second platelet detection data of the blood sample based on the large platelet region.

12. The non-transitory computer-readable storage medium according to claim 8, wherein the lytic reagent comprises a hemolytic agent for lysing red blood cells and a fluorescence dye for staining blood cells, and the two types of optical signals comprise scattered light signals and fluorescent signals, and the method further comprises classifying white blood cells into white blood cell subpopulations, or counting white blood cells or identifying nucleated red blood cells or immature cells or basophils according to the scattered light signals and the fluorescent signals; or the lytic reagent comprises a hemolytic agent for lysing red blood cells, and the two types of optical signals comprise first scattered light signals and second scattered light signals, wherein the first scattered light signals are forward scattered light signals, and the second scattered light signals are at least one type of medium-angle scattered light signals and side scattered light signals, and the method further comprises classifying white blood cells into white blood cell subpopulations or identifying basophils according to the first scattered light signals and the second scattered light signals.

13. The non-transitory computer-readable storage medium according to claim 8, the steps further comprising:
outputting the first platelet detection data if there is no alarm for abnormality; and
outputting the second platelet detection data if there is an alarm for abnormality.

14. The non-transitory computer-readable storage medium according to claim 8, the steps further comprising: continuously recording and counting comparison results of evaluation values of platelet detection for a plurality of blood samples, and providing an alarm for indicating that an abnormality is present in the electrical impedance signal detection when the continuous comparison results of the plurality of blood samples indicating the evaluation values being greater than the preset threshold.

* * * * *